(12) United States Patent
Choye et al.

(10) Patent No.: US 11,559,354 B2
(45) Date of Patent: Jan. 24, 2023

(54) SYSTEM AND METHOD FOR MICROABLATION OF TISSUE

(71) Applicant: LUMENIS LTD., Yokneam Ilit (IL)

(72) Inventors: Ray Choye, Belmont, CA (US); Vladimir Lemberg, Santa Clara, CA (US)

(73) Assignee: LUMENIS BE LTD.

( * ) Notice: Subject to any disclaimer, the term of this patent is extended or adjusted under 35 U.S.C. 154(b) by 296 days.

(21) Appl. No.: 16/805,796

(22) Filed: Mar. 1, 2020

(65) Prior Publication Data
US 2020/0315705 A1 Oct. 8, 2020

Related U.S. Application Data

(63) Continuation of application No. 14/964,987, filed on Dec. 10, 2015, now abandoned.

(51) Int. Cl.
*A61B 18/20* (2006.01)
*A61B 18/00* (2006.01)
*A61B 17/00* (2006.01)

(52) U.S. Cl.
CPC .. *A61B 18/203* (2013.01); *A61B 2017/00057* (2013.01); *A61B 2018/00452* (2013.01); *A61B 2018/00458* (2013.01); *A61B 2018/00577* (2013.01); *A61B 2018/00642* (2013.01); *A61B 2018/00994* (2013.01)

(58) Field of Classification Search
CPC ........ A61B 18/203; A61B 2018/00452; A61B 2018/00458; A61B 2018/00577; A61B 2018/00642; A61B 2018/00994; A61B 2017/00057
See application file for complete search history.

(56) References Cited

U.S. PATENT DOCUMENTS

| | | | |
|---|---|---|---|
| 4,408,602 | A | 10/1983 | Nakajima |
| 5,269,778 | A | 12/1993 | Rink et al. |
| 5,360,447 | A | 11/1994 | Koop |
| 5,713,902 | A | 2/1998 | Friedl |
| 5,843,079 | A | 12/1998 | Suslov |
| 5,908,417 | A | 6/1999 | Miller et al. |
| 5,957,915 | A | 9/1999 | Trost |
| 6,027,501 | A | 2/2000 | Goble et al. |

(Continued)

FOREIGN PATENT DOCUMENTS

| | | |
|---|---|---|
| EP | 1627662 | 2/2006 |
| KR | 20070044621 | 4/2007 |

(Continued)

OTHER PUBLICATIONS

Choi et al. "Analysis of Thermal Relaxation During Laser Irradiation of Tissue", Lasers in Surgery and Medicine, vol. 29, 2001, pp. 351-359.

(Continued)

*Primary Examiner* — Boniface Ngathi N
(74) *Attorney, Agent, or Firm* — ISUS Intellectual Property PLLC; Anthony Jason Mirabito

(57) ABSTRACT

The present invention generally relates to the field of laser treatment of tissue, and particularly, to a system and method for creating microablated channels in skin. The present invention is more particularly directed to treating subsurface tissue through the created channels.

11 Claims, 18 Drawing Sheets

(56) References Cited

U.S. PATENT DOCUMENTS

| | | |
|---|---|---|
| 6,099,522 A | 8/2000 | Knopp et al. |
| 6,110,195 A | 8/2000 | Xie et al. |
| 6,117,130 A | 9/2000 | Kung |
| 6,143,018 A | 11/2000 | Beuthan et al. |
| 6,152,918 A | 11/2000 | Padilla et al. |
| 6,159,204 A | 12/2000 | Hibst |
| 6,193,711 B1 | 2/2001 | Connors et al. |
| 6,328,733 B1 | 12/2001 | Trost |
| 6,402,739 B1 | 6/2002 | Neev |
| 6,482,199 B1 | 11/2002 | Neev |
| 6,527,716 B1 | 3/2003 | Eppstein |
| 6,595,987 B1 | 7/2003 | Negus et al. |
| 6,763,836 B2 | 7/2004 | Tasto et al. |
| 6,881,212 B1 | 4/2005 | Clement et al. |
| 6,902,562 B1 | 6/2005 | Negus et al. |
| 8,246,611 B2 | 8/2012 | Paithankar et al. |
| 2001/0016732 A1 | 8/2001 | Hobart et al. |
| 2002/0045811 A1 | 4/2002 | Kittrell et al. |
| 2002/0120260 A1 | 8/2002 | Morris et al. |
| 2002/0161357 A1 | 10/2002 | Anderson et al. |
| 2002/0183724 A1 | 12/2002 | Neev |
| 2003/0055418 A1 | 3/2003 | Tasto et al. |
| 2003/0083607 A1 | 5/2003 | Bobo, Jr. |
| 2003/0095266 A1 | 5/2003 | Detaile et al. |
| 2003/0149427 A1 | 8/2003 | Waner |
| 2003/0199859 A1 | 10/2003 | Altshuler et al. |
| 2003/0216719 A1 | 11/2003 | Debenedictis et al. |
| 2004/0024348 A1 | 2/2004 | Redding |
| 2004/0143248 A1 | 7/2004 | Marchitlo |
| 2004/0195221 A1 | 10/2004 | Haglund Jr et al. |
| 2004/0230258 A1 | 11/2004 | Altshuler et al. |
| 2005/0049582 A1 | 3/2005 | DeBenedictis et al. |
| 2005/0070896 A1 | 3/2005 | Daniel et al. |
| 2005/0154380 A1 | 7/2005 | DeBenedictis et al. |
| 2006/0004347 A1 | 1/2006 | Altshuler et al. |
| 2006/0007965 A1 | 1/2006 | Tankovich et al. |
| 2006/0058712 A1 | 3/2006 | Altshuler et al. |
| 2006/0079816 A1 | 4/2006 | Barthe et al. |
| 2006/0095103 A1 | 5/2006 | Eggers et al. |
| 2006/0149223 A1 | 7/2006 | Hwang et al. |
| 2006/0155266 A1 | 7/2006 | Manstein |
| 2006/0173447 A1 | 8/2006 | Jay |
| 2006/0217695 A1 | 9/2006 | DeBenedictis et al. |
| 2006/0241442 A1 | 10/2006 | Barthe et al. |
| 2006/0271028 A1 | 11/2006 | Altshuler et al. |
| 2007/0118098 A1 | 5/2007 | Tankovich |
| 2007/0239236 A1 | 10/2007 | Manstein |
| 2007/0264288 A1 | 11/2007 | Manstein |
| 2007/0264626 A1 | 11/2007 | Debenedictis |
| 2008/0071258 A1 | 3/2008 | Lemberg et al. |
| 2008/0208104 A1 | 8/2008 | Bragagna et al. |
| 2009/0112192 A1 | 4/2009 | Barolet et al. |
| 2009/0118720 A1 | 5/2009 | Black et al. |
| 2011/0208272 A1 | 8/2011 | Jay |
| 2011/0238141 A1 | 9/2011 | Webb et al. |

FOREIGN PATENT DOCUMENTS

| | | | |
|---|---|---|---|
| WO | 9113652 | 9/1991 | |
| WO | 9726830 | 7/1997 | |
| WO | 9938572 | 8/1999 | |
| WO | 02090036 | 11/2002 | |
| WO | 2006111199 | 10/2006 | |
| WO | WO-2008001284 A2 * | 1/2008 | ........... A61B 18/203 |

OTHER PUBLICATIONS

Laubach et al., "Skin Responses to Fractional Photothermolysis Lasers in Surgery and Medicine Issue 2" Feb. 2006, pp. 142-149 vol. 38, Publisher: Wiley-Liss Inc.

Manstein et al. "Fractional Photothermolysis: A New Concept for Cutaneous Remodeling Using Microscopic Patterns of Thermal Injury Lasers in Surgery and Medicine Issue 5", Jun. 2004 pp. 426-438 vol. 34.

McKenzie "A Three-Zone Model of Soft-Tissue Damage by a CO2 Laser" Phys. Med. Biol. Feb. 19, 1986, pp. 967-983 vol. 31 No. 9 Publisher: The Institute of Physics.

* cited by examiner

SYSTEM AND METHOD FOR MICROABLATION OF TISSUE

CROSS-REFERENCE TO RELATED APPLICATIONS

This application is a continuation of U.S. patent application Ser. No. 14/964,987, filed Dec. 10, 2015, which is a continuation of U.S. patent application Ser. No. 14/735,172, filed Jun. 10, 2015, which is a continuation of U.S. patent application Ser. No. 12/799,064, filed Apr. 15, 2010, now U.S. Pat. No. 9,078,680, granted on Jul. 14, 2015, which is a continuation-in-part of U.S. patent application Ser. No. 11/730,017 filed Mar. 29, 2007, now U.S. Pat. No. 8,496,696, granted on Jul. 30, 2013, which claims priority to U.S. Ser. No. 60/791,194, filed on Apr. 12, 2006, U.S. Ser. No. 60/850,628, filed on Oct. 11, 2006, and U.S. Ser. No. 60/832,964, filed on Jul. 25, 2006. These applications are incorporated by reference in their entireties.

BACKGROUND OF THE INVENTION

Field of the Invention

The present invention generally relates to the field of laser treatment of tissue, and particularly, to a system and method for creating microablated channels in skin. The present invention is more particularly directed to treating subsurface tissue through the created channels. By doing treating subsurface tissue through uniquely created channels, skin may be treated with heretofore unrealized results.

Description of the Related Art

Skin is primarily made of an outer layer, or epidermis, that has a depth of approximately 100/an from the outer surface of the skin and an inner layer, or dermis, that has depth of approximately 3000 fm from the outer surface of the skin. As used herein, "dermal tissue" or "skin" refers to both the dermis and epidermis layers.

There is ongoing demand for procedures to improve skin defects. Such improvements include reducing wrinkles, reducing dyschromia (a variety of abnormalities or irregularities of skin color resulting from, inter alia, irregular pigment distribution, dilated blood vessels, etc.) and etc. A wide variety of skin treating techniques have been introduced in recent years for attempting to achieve this objective. The skin treating techniques that have been employed may be generally categorized into two general types of treatment: ablative laser skin resurfacing ("LSR") and non-ablative collagen remodeling ("NCR"). LSR generally may result in fairly extensive thermal damage to either the epidermis and/or the dermis. NCR, on the other hand, is designed to avoid thermal damage of the epidermis.

Nevertheless, LSR is an effective laser treatment for treating skin. A typical LSR procedure comprises thermally damaging a region of the epidermis 100 and a corresponding lower region of the dermis 110 for promoting wound healing. Electromagnetic energy 120 is directed towards a region of skin, thereby ablating the skin and removing both epidermal tissue and dermal tissue. Combining LSR with a pulsed laser, for example a CO2 or an Er:YAG laser, is typically referred to as laser resurfacing or ablative resurfacing. This is considered to be an effective treatment protocol photo aged or chronically aged skin, scars, superficial pigmented lesions, stretch marks, and/or superficial skin lesions. Major drawbacks include, however, edema, oozing, and burning discomfort up to the first fourteen (14) days after treatment. Such drawbacks are unacceptable for many patients. A further problem with LSR procedures is that they are relatively painful. Therefore, they generally require an application of a significant amount of analgesia. While LSR of relatively small areas can be performed under local anesthesia, LSR procedures that include relatively large areas frequently require general anesthesia or nerve blockage by multiple anesthetic injections.

Another limitation of LSR is that ablative laser resurfacing generally cannot be performed on the patients having dark complexions. Ablation of pigmented epidermis tissue can cause severe cosmetic disfigurement to patients having a dark complexion. Such disfigurement can last from several weeks up to years. This is generally considered to be unacceptable by most patients and physicians. Yet another limitation of LSR is that ablative resurfacing generally has a greater risk of scarring in areas other than the face and result in an increased incidence of an unacceptable scar formation because the recovery from skin injury within these areas is not very effective.

Several NCR techniques have attempted to overcome the aforesaid problems associated with LSR procedures. These techniques may be variously referred to as non-ablative resurfacing, non-ablative subsurfacing, or non-ablative skin remodeling. Such NCR techniques generally use non-ablative lasers, flash lamps, or radio frequency current for damaging the dermal tissue and avoiding damage to the epidermal tissue. NCR techniques apply the concept that it is the thermal damage of the dermal tissues that is thought to induce wound healing. This results in biological repair and the formation of new dermal collagen which in turn can result in decreased photoaging related structural damage. Avoiding the epidermal damage by using NCR techniques may also decrease both the severity and the duration of treatment related side effects, for example, post procedural oozing, crusting, pigment changes, and the incidence of infections.

Treating skin using the NCR method involves heating selective portions of dermal tissue within the dermal layer for inducing wound healing without damaging the epidermis above. By cooling the surface of the skin and focusing electromagnetic energy, for example a laser beam, a selected dermal damaged region can be achieved while leaving the epidermis undamaged. Using non-ablative lasers for damaging the dermis while leaving the epidermis undamaged is common to NCR treatment methods. Generally, using non-ablative lasers result in deeper dermal penetration depths as compared to the ablative lasers than the superficially-absorbed ablative Er:YAG and CO2 lasers used in typical LSR procedures. Further, when NCR techniques are used, they generally do not have the undesirable side effects characteristic of the LSR treatment, such as the risk of scarring or infection. Examples of NCR techniques and apparatus are disclosed by Anderson et al. in U.S. Patent Publication No. 2002/0161357.

Although these NCR techniques may avoid epidermal damage, a major drawback of this method is its limited effectiveness. For example, this is significantly less improvement of photoaged skin or scars after the NCR treatment than when LSR ablative techniques is used. In fact, even when multiple NCR treatments are employed, improvement in the patient's skin is often far below expectations. In addition, improvement is often delayed for several months when a series of treatment procedures are used. Although NCR techniques have been found to be moderately effective for wrinkle removal, they have generally not been found to be effective for dyschromia.

Another problem with using a NCR technique is the limited the breadth of acceptable treatment parameters for safe and effective treatment of dermatological disorders. This is because NCR procedures generally rely on an optimum coordination of laser energy and cooling parameters. This results in an unfavorable temperature profile in the skin. An unfavorable temperature profile consequently results in either no therapeutic effect on one hand, or scar formation due to the overheating of a relatively large volume of the tissue, on the other.

A problem that is common to both ablative and non-ablative resurfacing procedures is that they do not significantly use keratinocytes, which play an active role in the wound healing response. Keratinocytes release cytokines when the keratinocyte is damaged. Cytokines encourage wound healing. For example, during ablative resurfacing procedures, keratinocytes are removed from the skin along with the epidermis. This removes keratinocytes entirely from the healing process altogether. During non-ablative procedures, keratinocytes, located in the epidermis, are not damaged at all and thus do not release cytokines for aiding the healing process.

Accordingly, there is now provided with this invention an improved system and method for treating skin that effectively overcomes the aforementioned difficulties and long-standing problems inherent in using either a LSR or a NCR procedure. These problems have been solved in a simple, convenient, and highly effective way by which to treat skin.

SUMMARY OF THE INVENTION

In one aspect, the invention provides a method for treating tissue using a laser system with pulsed light output comprising indicating by a user at least two of: (i) a desired total light output energy, (ii) a desired average light output power, or (iii) a desired duration of laser application. The method further includes controlling the laser by the system in order to achieve the selected conditions (i), (ii), or (iii) specified by the user, and directing the light output of the laser to the tissue to be treated over the desired duration.

Implementations of the invention may include one or more of the following features. The laser system has a control for power that may be used to produce a population inversion, wherein the control varies between on and off states, and a population inversion may be produced when the control is varied from an off state to an on state. The system may vary this control between on and off states at least four times in order to achieve the selected conditions (i), (ii), or (iii). The layer system may have at least two attenuating elements and the system may place at least one of these at least two attenuating elements in the path of the laser's output in order to achieve the desired energy or average power or duration. Implementations of the invention may also include one or more of the following features. The light output of the laser may be ablative during a portion of the time that it is directed to the tissue and non-ablative during another portion of the time that it is directed to the tissue. Light output of the laser may be directed to the tissue through a mirror, an optical fiber, a prism, or another optical element. As a result of the light output power being directed to tissue, a channel may be ablated in the tissue having a predetermined width and predetermined height. A thermal affected zone of predetermined volume and shape may be created proximate said channel. The tissue may have a surface through which the light output power passes and the thermal affected zone may have a cross section in a plane parallel to that surface, which increases in diameter with the plane's distance from that surface, such that, the diameter of the cross section increases with distance from that surface for a range of distances to the surface.

Implementations of the invention may further include one or more of the following features. The method may further comprise administering a treatment through the channel. The output light power may raise the temperature of at least a portion of the tissue into which it is directed above 100° C. The system may measure the laser's light output power. The measured light output power may be used in a feedback control system in order to decide when to change the control from an on state to an off state or vice versa. The desired average light output power may be no greater than about 10% of the maximum instantaneous light output power which the laser is capable of producing. The light output power may deviate by no more than 10% from the desired average light output power during at least about 90% of the time that the laser is producing light output in response to the user's setting. The system may select from a set of discrete attenuation values the attenuation closest to the desired level.

In another aspect, the invention provides a system for treating tissue with light comprising a laser with pulsed light output and a digital controller for the laser. The digital controller implements a user interface which permits a user to select at least two of: (i) a total energy to be applied to the tissue, and (ii) a duration of the application of light to the tissue, and (iii) a desired average power level to be applied to the tissue. The digital controller controls the laser's light output to achieve the conditions (i), (ii), or (iii) specified by the user.

Implementations of the invention may include one or more of the following features. The light with which the tissue is treated may have a wavelength of at least about 9 µm. The laser may be capable of producing a pulsed light output with at least about 200 W peak light power.

In further aspect, the invention provides a system for treating tissue with light comprising a laser with pulsed light output, an optical system for directing the light output of the laser to the tissue, and a digital controller for the laser. The laser comprises a pumping mechanism and a control for that mechanism which can be varied between an on state and an off state. Varying the control from the off state to the on state may produce a population inversion. The digital controller is programmed to vary the control from the off state to the on state and back to the off state a plurality of times. The light output power of the laser does not fall to zero between the first transition to the off state and the last transition to the on state.

Implementations of the invention may include one or more of the following features. The digital controller may be programmed to receive from a user at least one numerical value and to compute from the at least one numerical value a desired light output power. The average light output power of the laser between the first transition to the off state and the last transition to the on state may lie within about 10% of the desired light output power.

According to one aspect of the invention, a method for treating tissue is disclosed. The method comprises applying electromagnetic radiation to the tissue for ablating a channel therein having a predetermined width and predetermined depth. The method includes non-ablatively heating tissue on the bottom of the channel with electromagnetic radiation and creating a thermal affected zone of predetermined volume proximate said channel. According to another aspect of the invention, a system for treating tissue, is disclosed which comprises an electromagnetic radiation source and an electromagnetic radiation emitting device for applying the electromagnetic radiation to the tissue for forming a channel therein having a predetermined width, predetermined depth, and a thermal affected zone of predetermined volume proximate said channel.

As will be appreciated by those persons skilled in the art, a major advantage provided by the present invention is full control of: depth of treatment, the amount and placement of heat, and the amount and placement of channels. It is therefore an object of the present invention to rejuvenate skin and reduce wrinkles, scars, dyschromia and other conditions such as melasma and hyperpigmentation. It is another object to provide a channel with or without heat for delivery other therapy (vitamins, drugs, etc). Additional objects of the present invention will become apparent from the following description.

In a further aspect of the invention, a method for treating tissue using a laser system with pulsed light output is provided. In this method, a user indicates at least two of a desired total light output energy, a desired average light output power, or a desired duration of laser application. The system controls the laser in order achieve the selected conditions specified by the user and directs the light output of the laser to the tissue to be treated over the desired duration. The system may achieve the conditions with the aid of attenuating elements which it can place in the path of the laser's light output. Alternatively, the system may achieve the conditions by repeatedly turning on and off the power in the laser's pumping system, causing the laser's light output power to be maintained in the vicinity of a specified level.

The method and apparatus of the present invention will be better understood by reference to the following detailed discussion of specific embodiments and the attached figures which illustrate and exemplify such embodiments.

BRIEF DESCRIPTION OF THE FIGURES

The patent or application file contains at least one color photograph. Copies of this patent or patent application with color photograph(s) will be provided by the Office upon request and payment of the necessary fee.

A specific embodiment of the present invention will be described with reference to the following drawings, wherein.

DETAILED DESCRIPTION OF THE INVENTION

The following preferred embodiment as exemplified by the drawings is illustrative of the invention and is not intended to limit the invention as encompassed by the claims of this application. A system and method for treating skin is disclosed herein. In skin tissue, for example, proteins such as collagen reside in the dermal layer of the skin. The microchannel disclosed in an embodiment of the present invention may itself target and alter the collagen fibers within the dermis as an effective treatment for wrinkles of the skin.

Alternatively, an embodiment of the microchannel disclosed herein may create a passage through which targeted tissue is treated.

Figure 1:
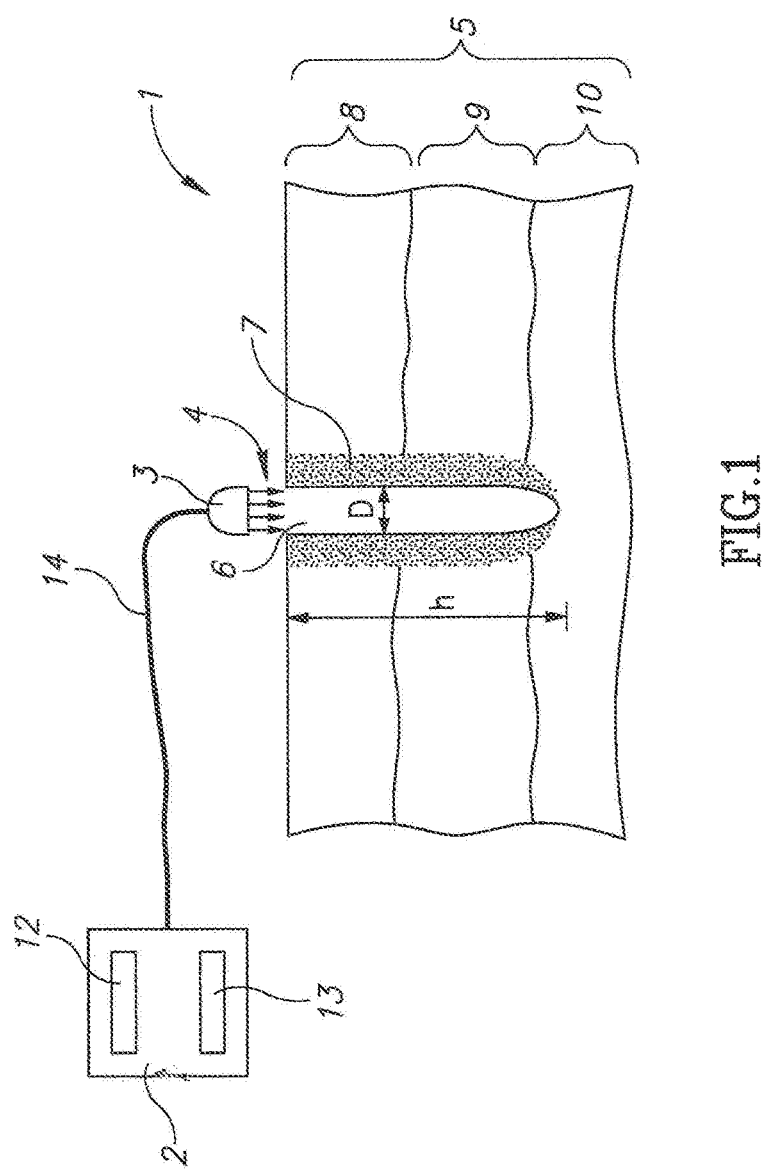
FIG. 1 is a schematic illustration of a microablation method and system in accordance with an embodiment of the invention.

As shown generally in FIG. 1, an embodiment of the present invention provides a system and method for performing microscopic ablation or partial microablation of e.g. tissue, and forming a microchannel through a surface of tissue to treat subsurface tissue. The microchannel may provide access to subsurface tissue targeted for a prescribed treatment, or the microchannel itself may provide a prescribed treatment. In some embodiments of the present invention, the microchannel may produce partial lateral denaturation of proteins (e.g. collagen) within the walls and/or at the bottom of the channel.

According to some embodiments of the invention, a tissue ablation system 1 may include a laser unit 2 and a laser emitting device 3 for ablating a microchannel 6 into a tissue 5, for example, for applying a treatment thereto as will be described below in detail. The microchannel 6 may be, e.g. a column, a well, a hole, or the like, created in the tissue 5 by ablating the tissue 5 by the laser emitting device 3 and the laser beam 4, for example, an ablating laser beam. Microablation of the tissue 5 may result in ablation of the microchannel. Microablation of the tissue may also result in dissipation of heat from the heated and evaporated tissue by the tissue surrounding the resultant microchannel 6. Thus, ablation of the tissue 5, producing the microchannel 6, may result in a thermal affected zone 7 surrounding the walls and/or bottom of the microchannel 6. The thermal affected zone 7 is generally indicative of damaged tissue and of tissue necrosis (the death of cells) in particular. As used herein, "damaged" is defined as inducing cell death in one or more regions of the dermal tissue of interest ("lethal damage"), or stimulating the release of cytokines, heat shock proteins, and other wound healing factors without stimulating necrotic cell death ("sublethal damage").

Selection of the laser beam 4 may also be based on the absorptive qualities of the tissue 5 to be treated. The absorptive properties of the tissue 5 to be treated may dictate or influence specific the type of laser or the characteristics of that laser suitable for a particular treatment for and/or microchannel. For example, certain lasers may reach depths unable to be reached by other types of lasers. As an example, an ablative laser may reach up to any depth required while non-ablative lasers may be unable to penetrate skin below, for example, about 50 pm. Similarly, it may be difficult to reach energy doses with one type of laser that are easily reached with others. Of course, as is well known in the art, if the wavelength is altered, the corresponding absorption level of the skin treatment area will be altered. Therefore, as long as the fluence described herein is maintained for achieving the microablation disclosed herein, different lasers having different characteristics may be used for achieving the same or similar results disclosed.

The microchannel 6 may be characterized by certain parameters, for example, diameter D and depth h. The diameter D of the microchannel and the depth h of the microchannel generally may be controlled by the energy characteristics of the laser. Such energy characteristics include, for example, wavelength, power, and the beam profile of the laser. Characteristics of the beam profile of the laser include, for example, pulse width, pulse duration, and pulse frequency). Furthermore, the profile and volume of the thermal affected zone may be formed by using different laser beam characteristics, such as chosen wavelength, energy of individual pulse or defined sequence of pulses, duration of each pulse, power distribution, shape of the laser spot, and the like, as will be outlined in detail below.

In some embodiments of the invention, the diameter of the ablated microchannel 6 may range from about 10 μm to about 500 pm, preferably in the range from about 50 pm to about 250 1.1 m. Microchannel diameter D may depend on the type of laser used and other parameters, for example, the elasticity of the skin. It has been found that the bottom of the formed microchannel is often conical due to the elastic forces of the skin as well as the power energy distribution of the spot formed by the laser.

The depth of the microchannel may be determined by the attending physician based upon the treatment required or selected by the physician. For example, treatment of collagen (collagen remodeling) typically located at a depth in the range from about 200 μm to about 2 mm from the surface of skin tissue may be desired. Treatment of blood vessels may necessitate a microchannel extending up to approximately 0.5 mm, which is where blood vessels are typically located. The microchannel 6 may therefore be created in accordance with an embodiment of this invention to a predetermined depth h to effect treatment to collagen or blood vessels or any other portion of the dermis selected by the attending physician. According to some embodiments of the present invention, the laser device 4 may produce the microchannel 6 reaching, for example, in the range from about 100 tm to about 3 mm in depth below the surface of the tissue 5.

Any suitable type of laser may be used, for ablating the microchannel, for example, $CO_2$ laser, Er:YAG, Tm:YAG, Tm fiber laser, Er fiber laser, Ho fiber laser, etc. or any other laser type as is well known in the art which may match a predetermined operational parameter such as, for example, optical absorption by tissue and intensity of laser that are strong enough to ablate small volumes with minimal lateral damage. The laser emitting device 3 may therefore be adapted for emitting an ablative laser beam 4 having any suitable power level and/or spot size and/or other associated characteristics. The laser power level may range, for example, in the range from about 0.5 mJ to about 250 mJ. The spot size of the laser beam 4 on the tissue surface may range, for example, in the range from about 10 p.m to about 50. For example, a $CO_2$ laser may use a spot size ranging from about 80 p.m to about 150 p.m for ablative treatment and preferably about 80 p.m.

In some embodiments of the present invention, the ablation may be produced by a continuous wave laser, by a single pulse of a laser, or by a series of pulses. The selection of these forms may depend, for example, upon the depth of the microchannel required, the diameter of the microchannel, as well as the size of the thermal affected zone, that is, the width of the lateral damage. In an embodiment using a continuous wave laser, for example, an ablating laser operating in a wavelength of 10.6 nm, the laser emitting device 3 may be operated at a power level of, e.g., in the range from about 1.0 W to about 250 W for a duration of, e.g., in the range from about 0.02 msec to about 500 msec. In an embodiment using a pulsed $CO_2$ laser, for example, a series of, for example, 10 pulses, each having a duration of, for example in the range from about 0.05 msec to about 100 msec may be fired at an energy level of, e.g. in the range from about 0.2 mJ to about 20 mJ. In an embodiment using a pulsed laser, a series of pulses, each having a duration of from about 0.05 msec to about 100 msec may be fired may be fired at an energy level of in the range from about 0.2 mJ to about 20 mJ. In skin, for example, applying a pulsed laser as indicated above may result in a microchannel 6 of a diameter in the range of from about 80 tm to about 100 gm, a depth in the range of from about 300 1-ffil to about 500 gm, and a thermal affected zone of lateral width in the range of from about 20 gm to about 300 gm. Additionally, as described below in an embodiment of the invention, a series of pulses, of pulsed laser may be fired at the tissue 5 to further deepen the microchannel 6, created as identified above. The microchannel 6 may be deepened to a desired depth, preferably to the level of the tissue to be non-ablatively treated. It should be noted that the diameter of the deepened microchannel 6 may be in the same range or different range as the previously created microchannel in the same location.

In some embodiments of the invention, the microablation channel 6 may be sculpted by employing different pulse characteristics of the laser beam. Pulse characteristics of a laser beam, e.g. laser beam 4, may further include different energy profiles. As mentioned above, the depth h of the microchannel and the resulting width of lateral damage and the profile of the thermal affected zone 7 may be controlled by different laser beam characteristics. For example, the laser beam 4 may have characteristics resulting in the thermal affected zone 7 having a substantially constant width (linear profile) 7. It will be recognized that some embodiments of the invention may have a thermal affected zone 7 profile different from the one depicted in FIG. 1. Furthermore, it is now possible to produce a microchannel 6 according to embodiments of the present invention with a minimal thermal affected zone 7, e.g. a width in the range from about 1 gm to about 5 liM with the use of the Er:YAG laser.

In some embodiments of the present invention, the laser unit 2 may include a controller 12 able to control the laser emitting device 3, and an input interface 13 capable of receiving input parameters from user of system 1. Such input parameters may be for defining microablation treatment parameters, for example. User input parameters to the interface 13 may further include the microchannel depth, the spatial location of the microchannel 6 on the tissue surface 1, etc. Parameters may be provided at the input interface 13 by an operator of the system, for example, a physician, or alternatively, through an imager program detailed below. The controller 12 may be able to perform at least one of the following functions, as will be described in more detail below: (a) identifying at least one location for treatment; (b) selecting treatment(s) for each of at least one location; (c) operating a laser and directing mechanism to produce the at least one microablation; and (d) delivering the selected treatment(s) at the at least one site.

Figure 2A:
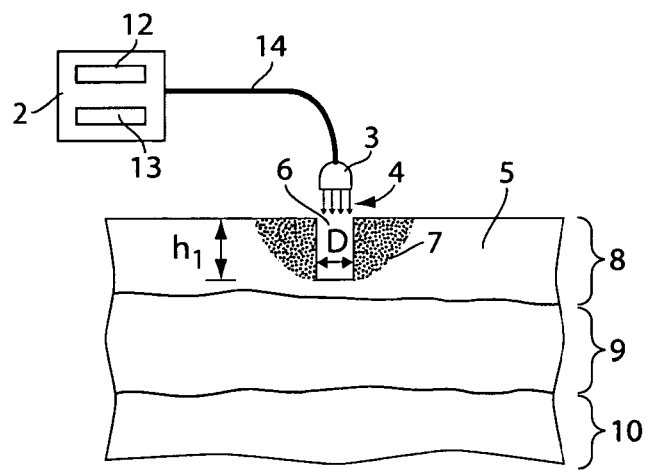
FIGS. 2A, 2B, 2C, and 2D are schematic illustrations of sequential stages of microablation and treatment in accordance with an embodiment of the invention.
Figure 2B:
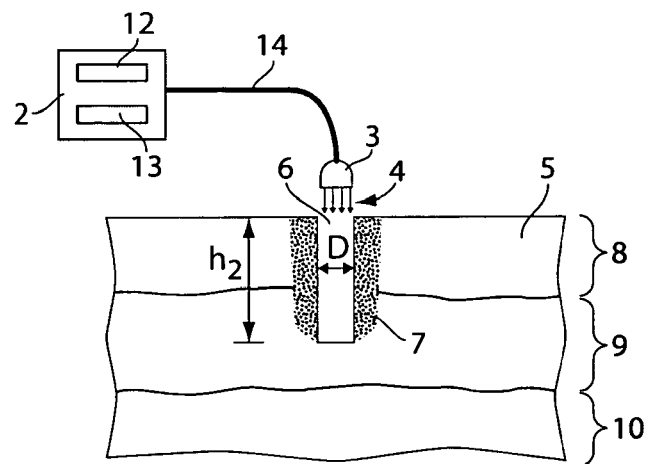
Figure 2C:
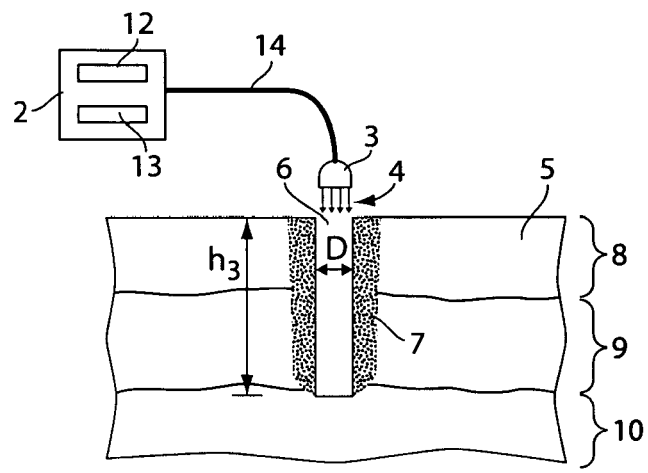
Figure 2D:
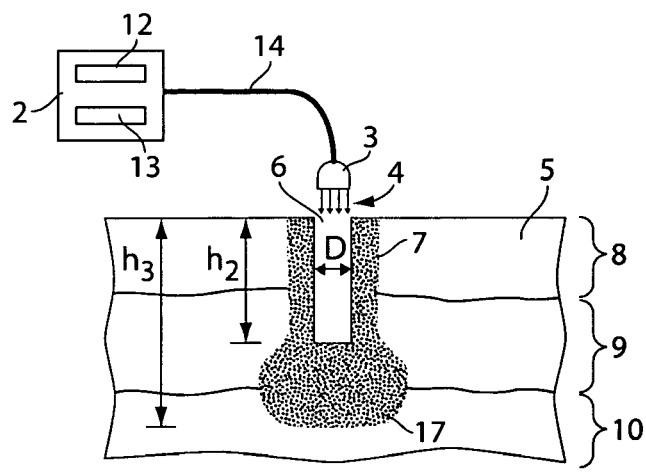

Reference is now made to FIGS. 2A, 2B, 2C, and 2D which schematically illustrate sequential stages of microablation and treatment in accordance with an embodiment of the invention. According to an embodiment of the invention, it may be desirable to apply treatment to tissue which may be, for example, in the hypodermis 10 in a way that substantially maintains the profile of the thermal affected zone throughout the treatment protocol. As it is desirable to minimize the necrosis of tissue at the surface 11, it may be beneficial to apply a plurality of laser pulses onto the tissue 5 in order to reach a depth of treatment area in the hypodermis 10. As illustrated in FIG. 2A, the microchannel 6 created by a first ablative laser pulse, may have the desired thermal affected zone 7, e.g. linear profile of constant width, for example, a minimal width, and may have a depth of h1 that is not sufficiently deep to provide treatment to the hypodermis 10. A second ablative laser pulse may be applied through microchannel 6 of FIG. 2A to deepen the microchannel 6 having a minimal thermal affected zone to a depth h2 into, for example, the dermis 9 of the tissue 5, while maintaining the predetermined minimal thermal affected zone profile, as illustrated in FIG. 2B. Finally, as indicated in FIG. 2C, a third ablative laser pulse may be applied through the microchannel 6 of FIG. 2B to deepen the microchannel 6 having a minimal thermal affected zone 7 further to a depth h3 into the targeted hypodermis layer 10, while maintaining the predetermined thermal affected zone profile 7. Alternatively, if a non-ablative pulse is applied after the profile depicted in FIG. 2B, the profile may appear as depicted in FIG. 2D. According to some embodiments of the invention, a delay representing a minimum time, e.g. 1 to 100 msec, may pass between each laser pulse, thereby allowing relevant portions of tissue 5 to cool down between each pulse. This delay may be between any succession of laser pulses whether they are ablative or non-ablative. It is preferable to have a delay after an ablative laser pulse. To allow for cooling of tissue 5, the minimum time between pulses may be determined according to, for example, a predetermined tissue relaxation time which may define, e.g. the time required to dissipate a certain amount of heat absorbed by, e.g. the tissue 5, during a laser pulse applied by the laser device 3. The delay may also allow venting of ablative tissue and or gases that may have developed during an ablative pulse of light. Accordingly, if a time of an applied pulse is shorter than the tissue relaxation time and the beam has a top hat profile a very low amount of heat may dissipate through walls of the microchannel 6.

A beam profile that would conform to an inverted top bat may be preferable in some embodiments of the present invention for forming a channel with well defined side walls, minimal microchannel diameter, and a minimal thermal affected zone. Typically, a beam has a Gaussian power distribution across the diameter of its spot. Since the power on the edges of such a spot is less than the power in the center of the spot, it is often difficult to form a straight walled channel or hole. By having a beam profile that has a uniform power distribution across its spot (a top hat profile) it will be easier to form a straight walled channel.

In some embodiments of the invention, upon producing the microchannel and clearing a path to the treatment site, a wide variety of types of treatment may be delivered to the site, as detailed below. In some embodiments, the treatment may be non-ablative laser treatment. Such non-ablative laser treatment may be used, for example, for remodeling collagen. As is more particularly illustrated in FIG. 2D, a non-ablative laser treatment may be delivered to the tissue 5 in the dermis 9 after the microchannel 6 has been created. The path created for the non-ablative heating of the target tissue may follow embodiments of the invention detailed above regarding FIG. 2A, or 2B and/or 2C. That is, heating of subsurface tissue by a non-ablative laser through the created microchannel may be through a microchannel that was created by one or by more that one ablative pulses. Laser treatment by the laser beam 4 may be applied to the tissue 5 in the dermis 9, whereby the tissue 5 is heated to a temperature below that at which the tissue is ablated though heated to a temperature sufficient to denature collagen, for example, in the range of from about 50° C. to about 67° C. The non-ablative laser beam 4 may further create a thermal affected zone of denatured collagen 17, without tissue ablation, whereby collagen is heated. The collagen thereupon contracts, thus removing wrinkles. The non-ablative laser beam 4 may further be applied to targeted tissue for removing pigmentation, treating blood vessels, and other treatments, as is well known to those skilled in the art.

Accordingly, it will be appreciated that the use of the microchannel 6 of the present invention as a conduit for applying non-ablative heat to targeted subsurface tissue, enables the heating of the subsurface tissue to be treated without excessively damaging non-targeted tissue, for example, the surface tissue. Further, the thermal affected zone may be additionally controlled by having non-ablative heating applications interposed between ablative treatments for creating a larger thermal affected zone 17 deep in the tissue, for example in the dermis 9.

Figure 3A:
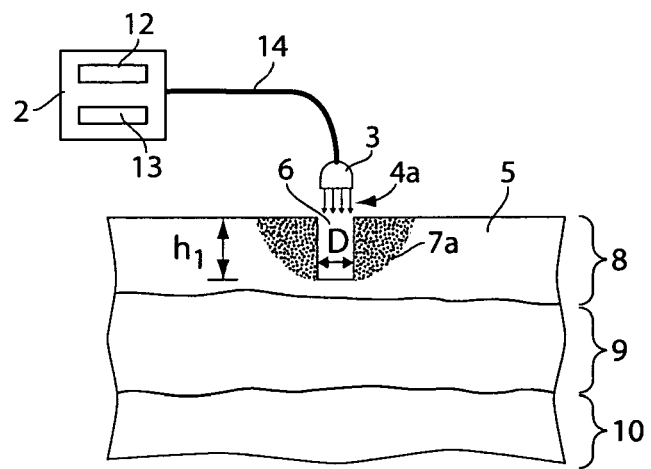
FIGS. 3A, 3B, 3C, and 3D are schematic illustrations of sequential stages of microablation in accordance with an embodiment of the invention.
Figure 3B:
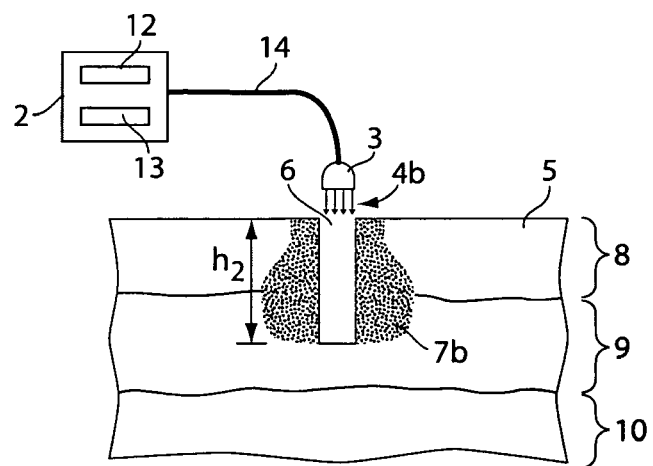

Reference is now additionally made to FIGS. 3A, 3B, 3C, and 3D which schematically illustrate sequential stages of treatment in microablation channels in accordance with embodiments of the invention. In accordance with to some embodiments of the invention, it may be desirable to create a predetermined non-uniform thermal affected zone profile and/or lateral width damaged area along the depth of the channel. In other embodiments of the invention, an area of tissue in the dermis 9 may be, treated for forming a predetermined thermal affected zone having a profile different from the profile of the thermal affected zone in the epidermis 8 near the surface. As is more particularly illustrated in FIG. 3A, the microchannel 6 having a predetermined thermal affected zone and/or profile 7a and a depth h1 may be created by a first ablative laser pulse. As illustrated in FIG. 2D, a second laser non-ablative laser pulse may heat the bottom of the microchannel 6 thereby damaging a spherical area surrounding the bottom of the channel to a depth h3, reaching for example, beyond the dermis 9. This second pulse may have different characteristics than the first pulse, producing a thermal affected zone having a different area and/or profile than the first pulse and resulting in the profile illustrated in FIG. 2D. When a second ablative laser pulse (that is, the third pulse to this treatment area) is applied through the damaged tissue on the bottom of the microchannel, a profile 7b as depicted in FIG. 3B is formed. Thus, FIG.

Figure 3C:
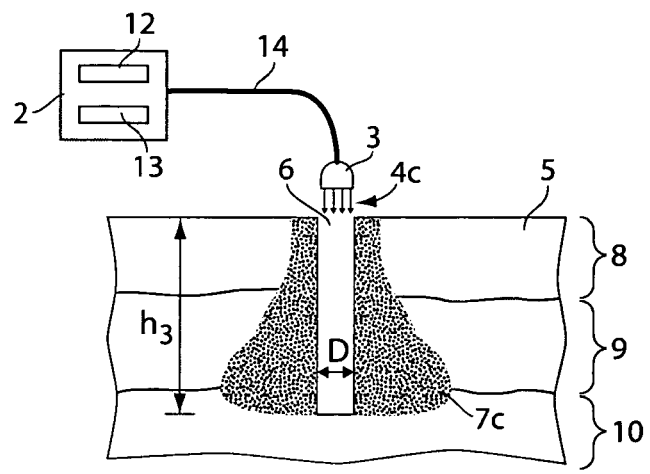
Figure 3D:
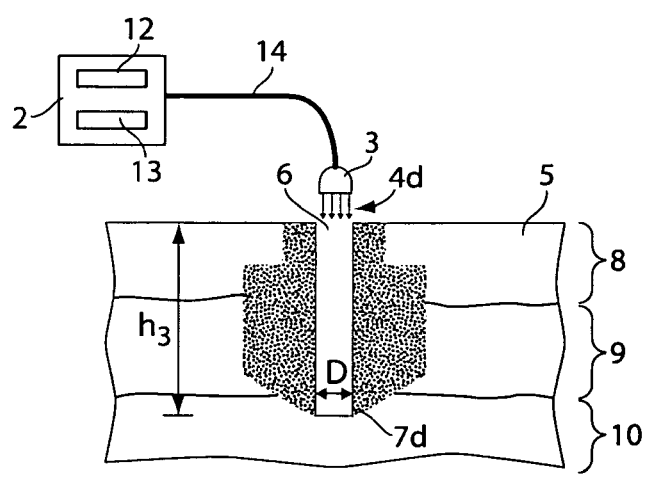

3B depicts an ablative laser pulse applied subsequent to the non-ablative laser pulse which formed the profile depicted in FIG. 2D. Alternating ablative laser treatment with non-ablative laser treatment may result, for example, in a microchannel having a thermal affected profile as illustrated in FIG. 3C. It will be understood that a microchannel may be produced to any depth and by any number of pulses for creating a series of predetermined thermal affected zones that may vary along the depth of the microchannel. In this way, a predetermined thermal affected zone profile along the microchannel 6 is formed. It is thus possible to build a variety of predetermined thermal affected zone areas and/or profiles along the wall and/or the bottom of the microablated channel, using a sequence of pulses with different parameters (e.g. energy and duration or wavelength) and employing the natural thermal conductivity of tissue. For example, in another embodiment of the invention, an ablative laser pulse applied to the tissue 5 may have characteristics producing a thermal affected zone having an area and/or profile 7d as illustrated in FIG. 3D. The thermal affected zone 7d in FIG. 3D illustrates that the thermal affected zone area may decrease along the depth of the channel, according to predetermined laser beam parameters. Of course, once the depth of the tissue targeted for treatment is reached, the non-ablative heating of the tissue should preferably commence.

In some embodiments of the present invention, the creation of the microchannel 6 with the desired thermal affected zone profile 7 along the walls and/or bottom of the microchannel 6 may itself be the desired treatment method. Additionally or alternatively, creating the microchannel 6 itself may facilitate the desired treatment method, by providing access directly to a subcutaneous site for treatment. For example, upon completion of the microchannel, a substance may be delivered to the treatment site by any means, including for example, ultrasonic delivery. Additionally or alternatively, the microchannel may serve as a conduit for transdermal substance delivery, for example, for diffusion, electrophoresis, ointments, acids, healing substances, chemical peeling agents, collagen modification agents, fillers, stem cells, or any variety of administering medicines and the like. It will be noted that the depth of the microchannel need not be the only or even the primary treatment site; rather the treatment site may be any and all sites along the walls and/or bottom of the microchannel adjacent to or proximate the microchannel.

In some embodiments of the invention, the controller 12 may provide 3 a command via a signal 14 to the laser device for applying a pulse or series of pulses to the tissue 5. The controller may provide a variety of commands to the laser device 3, for example, the sequence and duration of pulses to apply to the tissue 5. The controller may also select form a variety of laser sources for applying a desired sequence of ablative and non-ablative laser applications to a particular site. The controller may also prescribe the desired delay between the laser applications. Furthermore, the controller 12 enables the laser emitting device 3 to deliver precise multi-spot ablation to selective portions of tissue in accordance with preselected treatment protocols as is well known by the physician.

In some embodiments, more than one microchannel may be produced substantially concurrently or in rapid sequence on the tissue 5, for example, by directing the laser emitting device 3 from one predetermined site to another of the tissue 5, applying a pulse at each site and returning precisely to the previously treated site so as to apply the next pulse in the sequence. Thus, while the tissue 5 at one microchannel is cooling, the controller 12 may send a command to the laser device 3 to move among one or more sites on the tissue 5 for creating a plurality of microchannels at a plurality of sites. Such a device may use, for example, a laser scanner. Such scanners may operate in accordance with the teachings in U.S. Pat. Nos. 5,713,902; 5,957,915; and 6,328,733, all of which are incorporated herein by reference. For example, at a first scanning sequence, the laser device 3 may provide the laser beam 4 on the first site resulting in a microchannel of depth h1. The controller 12 may then move the laser device 3 to a second site to produce thereon a microchannel having a depth h1. This process may continue until the laser device 3 performed on each location has a microchannel resulting in depth h1. The controller 12 may then proceed to provide the laser beam 4 on a microchannel site further ablating a microchannel resulting in another microchannel of depth h2 directly below the first microchannel site. Alternatively, the second laser application may be a non-ablative laser beam. The controller 12 may then move the laser device 3 to a second site to produce a microchannel of depth h2. This process may continue until the laser device 3 performed on each microchannel location of depth h1 a second laser beam pulse resulting in a microchannel of depth h2. Of course, the order of the second beam across the selected treatment sites may be in a different order or sequence than the first pass. Alternative scanning sequences may apply laser beam pulses repeatedly at a location, then moving to another location to apply laser pulses. It may not be necessary that the same series of pulses (characteristics including duration and power) be applied at each location in the sequence and any number of series of pulses may be applied to tissue at various locations.

In some embodiments of the invention, the tissue 5 may be manipulated and the laser emitting device 3 positioned for applying the laser beam 4 to the tissue 5. For example, the skin tissue to be treated may be lifted and the laser beam 4 may be applied from the side. Furthermore, the controller 12 may direct the laser emitting device 3 to apply the laser beam 3 to the tissue 5 from a variety of angles from the perpendicular.

Figure 4A:
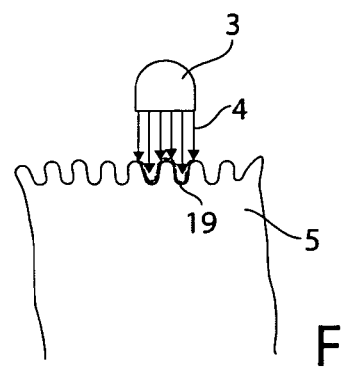
FIGS. 4A, 4B, 4C, and 4D are schematic illustrations of tissue manipulation in accordance with an embodiment of the invention.
Figure 4B:
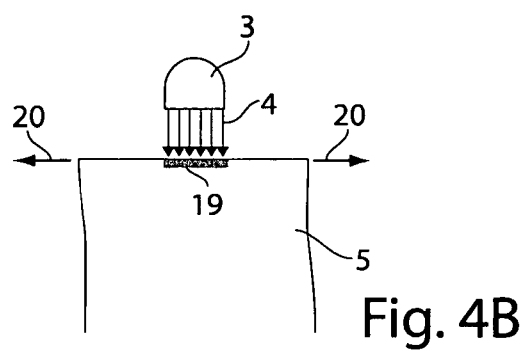
Figure 4C:
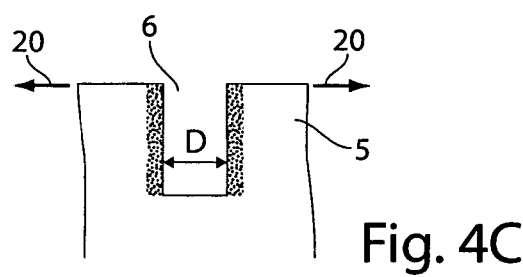
Figure 4D:
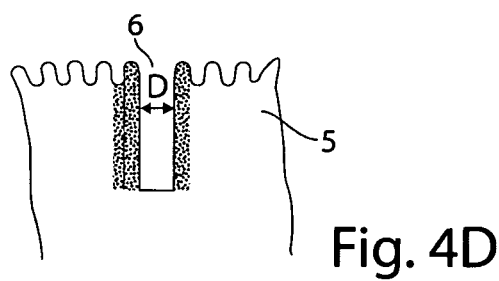

In another embodiment of the invention, it may be desirable to increase the amount of radiation per unit of surface area of the tissue 5. For example, the tissue 5 may be stretched prior to applying laser beam 4 to the tissue. Referring to FIG. 4A, laser beam 4 may be applied to unstretched tissue 5 over a surface area 19 of tissue. The tissue 5 may be stretched in a variety of directions as selected by the physician, for example, the lateral direction, manually or by some device applying a stretch 20, prior to producing the microchannel 6 as detailed above in an embodiment of the invention. Referring to FIG. 4B, applying stretch 20 to the tissue 5, effectively increases the amount of radiation per unit surface area 19 of the tissue 5. The microchannel 6 (FIG. 4C) created in the stretched tissue 5 will possess dimensions and characteristics as detailed above. Release of the tissue stretch 13, may result in a relaxed tissue 5 wherein the microchannel 6 now possesses a smaller diameter D' (i.e. D'<D; Ref. FIG. 4D). The reduction in microchannel diameter may also be a function of tissue properties, for example, tissue elasticity, tissue hydrated conditions, and the thickness of the stratum corneum. Thus, by stretching the skin prior to a laser beam is applied, the area of damaged skin may be further reduced. Stretching the skin has many advantages beyond just minimizing the amount of damaged skin. For example, by stretching the skin during the application of an ablative laser for creating a microchannel, the diameter of the microchannel will be further reduced. In this way, infection has a smaller entrance point and the chance for infection may be further minimized. Stretching the skin during the application of the laser beam (both an ablative laser beam and a non-ablative laser beam) provides additional advantages, for example, better penetration, better evacuation of vapors, and being less sensitive to the position of the target relative to the applied beam.

The system may also include an imager to enable a user to view the tissue area and to choose a treatment site. For example, the imager and an image processor may be used to determine the wrinkle topology of a tissue. For example, by using the imager combined with the application of polarized light, the outline, depth, and profile of the skin's topology may be more precisely determined. The wrinkle topology may be provided to the input interface 13 to communicate with the controller 12 and send a signal 14 to the laser device 3 to maximize the aim of the laser device 3 to the target tissue 5. The wrinkle topology may be used to measure the effectiveness of the treatment as well as used for identifying targeted sites that may require additional treatment.

An imager may also be used to generate optical feedback, either manually to the eye of the user, or automatically to an image processor, in order to return the laser to a previously treated site. The processor may process the image obtained from the imager for providing information to the controller for varying the treatment locations, the particular laser to be used, the laser spot size, the spot location, etc. In this manner, if the patient moved between pulses, an imager and processor may enable returning the laser to the precise site of the previous pulse. Use of an imager to optically track or determine tissue position may be used in concert with the process described above of the sequential creation of microchannels, as is well known to those skilled in the art.

Figure 5:
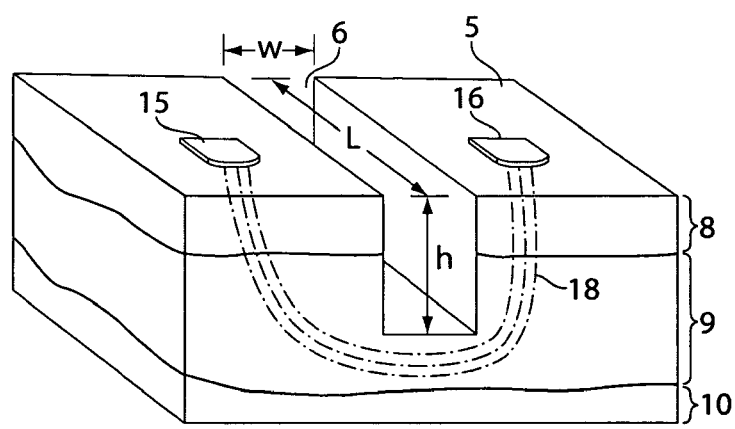
FIG. 5 is a schematic illustration of tissue treatment according to an embodiment of the invention.

As shown in FIG. 5, in another embodiment of the invention, the microchannel may be used to facilitate treatment to subcutaneous tissue by a means other than through the microchannel itself. The void of the microchannel may act as a barrier, or insulating separation of air, between layers of tissue on either side of the microchannel. Therefore, a microchannel may be used in conjunction with radio frequency (RF) energy treatment to allow driving a current below the microchannel. As illustrated, the microchannel 6 is created according to an embodiment of the present invention detailed above, having a width W, a length L, and a depth h. In this embodiment, the microchannel depth h reaches into the dermis of the tissue and the targeted tissue is beneath the microchannel 6 in the dermis 9.

Radio frequency electrodes 15 and 16 may be applied to the tissue at opposite sides of the microchannel 6. When RF current 18 is applied, the insulating (non-conducting) property of the microchannel 6 requires the current to flow between electrodes 15 and 16, below the microchannel depth h, directing the current to deeper tissue than would have occurred in the absence of the microchannel 6. The length L of the microchannel should preferably be at least twice its depth (2D) so that the applied current may go through the targeted tissue and not find an alternate path of less resistance. The length of the microchannel in this embodiment of the invention may be in the range of from about 100 pm to about 500 iirn, and preferably about 300 gm. Accordingly, it will be appreciated that by using the microchannels of the present invention, the heating of deeper layers of tissue may be achieved without damaging the surface tissue. It will further be appreciated that controlling the dimensions of the microchannel, e.g., the depth, width, and/or length of the microchannels may define the treatment provided by the treatment device, e.g., the RF electrodes, to the treatment layer of the tissue. It will be noted that by concentrating the current, the microchannel may provide for increased current density at the desired treatment site. A similar approach may be used for heating and followed shrinkage of collagen fibers at a predetermined depth.

Creating a microchannel into the tissue for reaching an area of targeted treatment may also be achieved without an ablative laser. For example, a microchannel may be created mechanically with a heated microneedle. After the microchannel is thus formed, non-ablative treatment may be applied.

Figure 6:
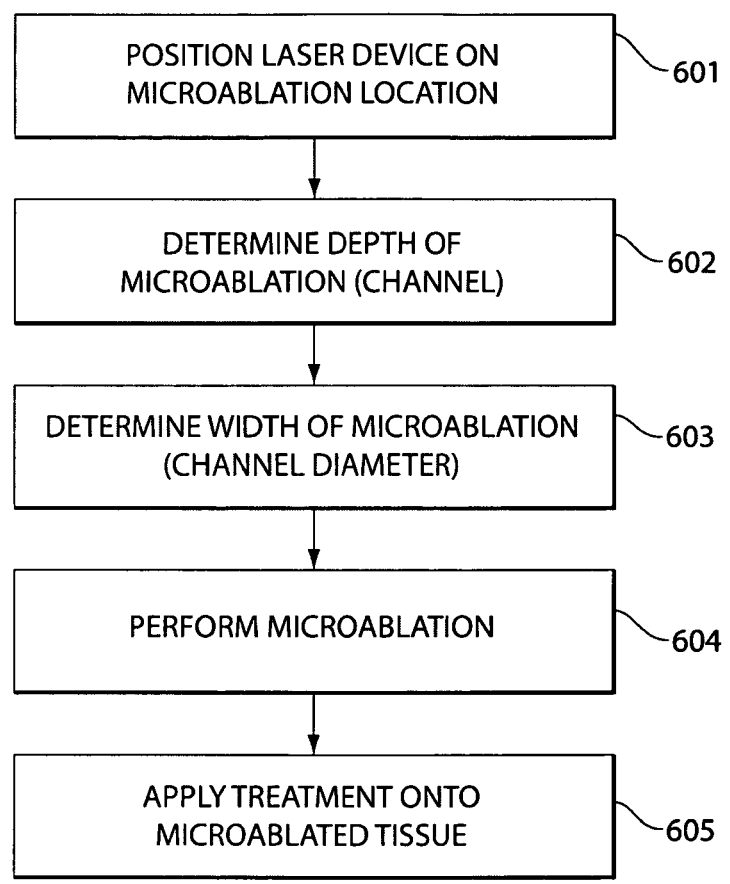
FIG. 6 is a schematic flow chart of a method of producing microablation on a tissue in accordance with an embodiment of the invention.

Reference is now made to FIG. 6, which schematically illustrates a flow-chart of a method for performing microablation on a tissue in accordance with an embodiment of the invention. As indicated at block 601, the method may include, for example, positioning the laser device for performing microchannel ablation. For example, the user of the system 1 may initially position the laser device 3 relative to the skin 5 to enable creating the microchannel at a desired location. As indicated at block 602, the method may also include, for example, determining the depth of the microchannel. For example, the user may determine that the desired depth of the microchannel 6 (FIGS. 2A, 2B and 2C) is h3. As indicated at block 603, the method may also include, for example, determining the width of the microchannel and/or the thermal affected zone. For example, the user may determine that the desired width of the microchannel 6 is D (FIG. 1) and the desired thermal affected zone profile may vary as in 7a, 7b, 7c, and 7d (FIGS. 3A, 3B, 3C and 3D). The density of microchannels (e.g., number of channels per area) can also be determined. The wavelength for the different stages of the ablation may also be determined. As indicated at block 604, the method may also include, for example, producing a microchannel. For example, the laser device 3 may emit a laser beam and may thereby produce the microchannel 6 in the tissue 5. As indicated at block 605, the method may also include, for example, applying treatment onto a microchannel location. For example, applying heat treatment to affect collagen at bottom of microchannel 6 (FIG. 2D). It will be recognized that the step of applying treatment is optional and need not be practiced in every embodiment of the invention.

Figure 7:
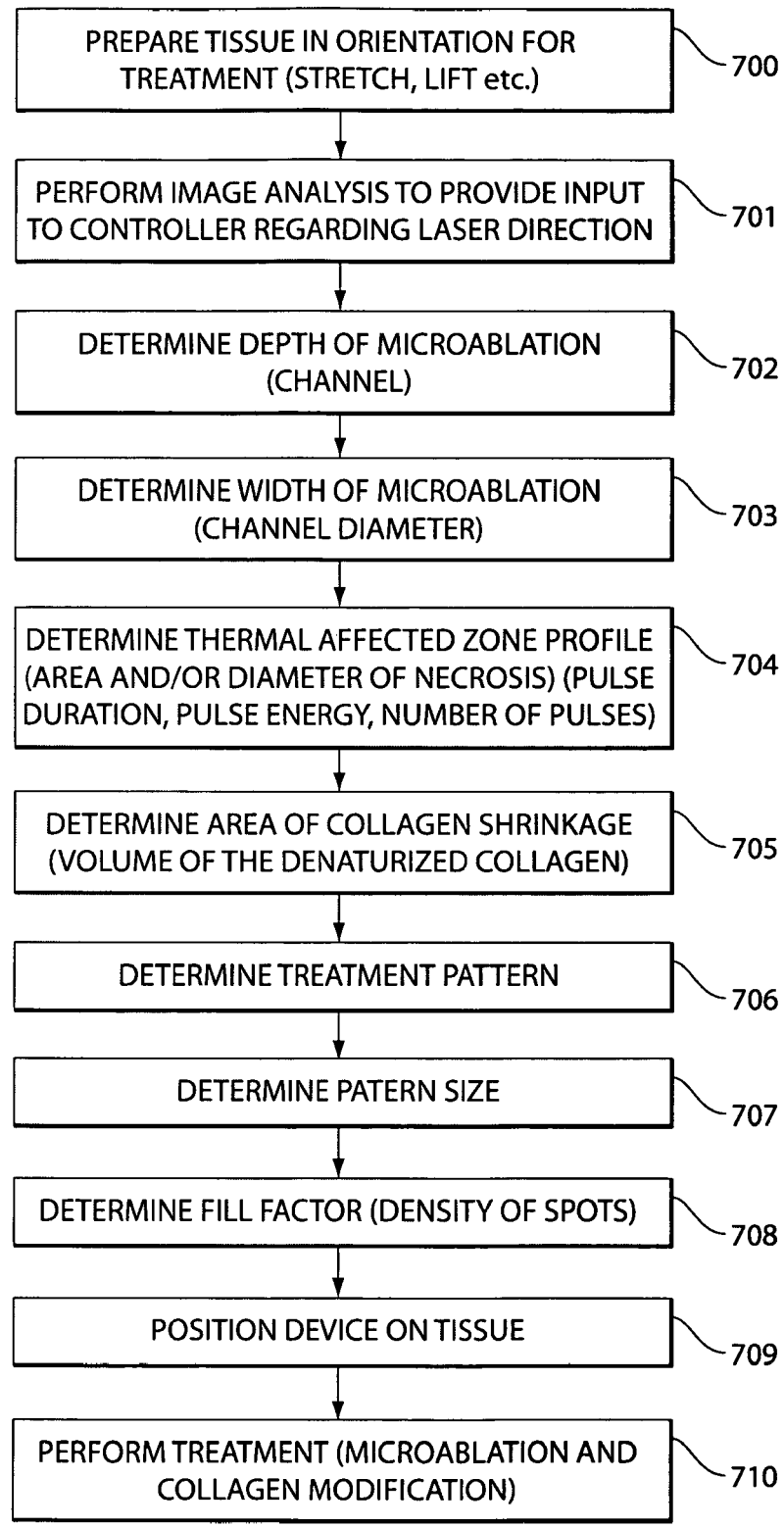
FIG. 7 is a schematic flow chart of a method of producing microablation on a tissue in accordance with an embodiment of the invention.

FIG. 7 depicts a flow chart method in accordance with embodiments of the present invention. At block 700, the orientation of the tissue 5 is selected for treatment, the tissue, e.g. skin is stretched, lifted, or left natural. At block 701, image analysis of the tissue surface is performed, for example, to create wrinkle topology, to provide information to the controller 12 (FIG. 1) in order to maximize laser orientation. It will be recognized that the step of image analysis is optional and need not be practiced in every embodiment of the invention. At blocks 702 and 703, the depth and width of the microchannels may be determined respectively, for example, based on the treatment program selected or selected by the operator. At block 704, the thermal affected zone (e.g. area and/or diameter of necrosis) may be determined, for example, by setting the pulse duration, pulse energy, the number of pulses, or the density of the pulses based on the treatment program, or based on selection by the operator. At block 705, the area of collagen shrinkage (i.e. thermal affected zone 17) may be determined (FIG. 2D). At block 706, a treatment pattern or program may be determined, for example, by the operator of the device selecting an appropriate program. At block 707, the size of the microchannel pattern may be determined, for example, automatically by scanning, or based on the treatment program, or by an operator selecting the appropriate pattern size. At block 708, the fill factor, for example, the density of the microchannels on the tissue, may be determined, for example, automatically by the device, e.g., based on the treatment program, or by selection by the operator of the device. At block 709, the device may be positioned on the tissue, and at block 710, the treatment may be performed by forming the microchannels, and/or applying any other desired treatment.

In a further aspect of the invention, systems are provided for control of the lasers used in microablation. As is well known lasers comprise a laser medium, a pumping system to generate a population inversion in the medium, and optics to pass certain photons repeatedly through the medium and to allow a usually narrow beam of light to exit the medium. The pumping system may be, for example, a set of electrodes and associated controls which create a glow discharge in a gas by supplying DC or RF energy to the gas, with the discharge producing a population inversion. For background on lasers see generally Jeff Hecht, Laser Guidebook (2nd ed. 1992) and Orazio Svelto, Principles of Lasers (David Hanna trans. 4th ed. 1998).

Figure 8:
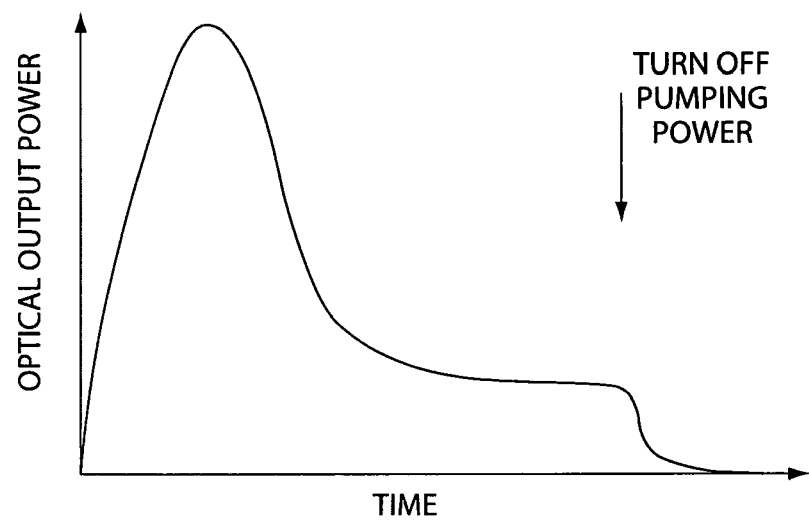
FIG. 8 depicts exemplary optical power output versus time curve for a laser system having pulsed output which is useful in microablation.

In systems for laser microablation one may advantageously, for example, a $CO_2$ laser in which initiation of laser action produces a high optical power output pulse, for example having a peak output power of 300 W. An exemplary optical power output of such a system over time is shown in FIG. 8. Lasers having pulsed optical output suitable for laser microablation have been marketed by the assignee of this application, for example, under the name UltraPulse®. The assignee's laser products include RF excited slab $CO_2$ lasers of the waveguide type.

In existing systems for laser microablation it is common to present the user (normally a physician) with an interface whereby the user chooses an output energy. This energy may, for example, be on the order of tens of millijoules, for example in the range of about 5 mJ to about 50 mJ.

A microablation system could provide the desired number of millijoules in the following manner. As part of the system design, one determines a curve of the light power output over time of the laser when a predetermined voltage step waveform is applied to the pumping system. On the basis of that curve, for a series of time values t one calculates the area under the curve from time 0 (onset of voltage applied to pumping system) to time t. That area under the curve will represent the amount of light energy that the system will output if started at time 0 and shut down at time t. From the series of areas under the curve for time values t, one can calculate by interpolation for any desired energy output a time value which will produce that energy output. Thus, for any energy, the system can calculate how long to apply power to the pumping system to produce that energy.

Alternatively, the system could start the application of energy to the pumping system and measure the light output power of the system. The system could integrate the light power output of the system over time (e.g., using some numerical integration algorithm) and turn off the energy input to the pumping system when the integrated power since turn-on reaches the desired energy level. The system might take into account the turn-off transient of the light power output when the pumping system shuts down and so shut down slightly short of the desired energy to compensate for that transient.

It is desirable to extend the capability of such systems whereby the user chooses both a desired amount of light energy and a duration over which the energy is applied. With this capability, the system described above based on the integrated optical power output would potentially not be adequate because it might have to stop short of the user's selected duration in order to meet the total energy constraint.

It is therefore desirable to have the ability to reduce reliably the output light energy level of the laser being used, even when it employs a roughly fixed input energy level to the pumping system and has a roughly fixed light power output curve as a function of time when that fixed input energy level is applied to the pumping system.

Given the curve of output light energy versus time described above, the system can calculate the degree of attenuation necessary to achieve both the desired energy output and the desired duration of action t. The system can, for example, determine the duration tfull to produce the desired energy output without attenuation, and then attenuate by tfulit to deliver the desired energy output over the chosen interval.

There are a number of reasons why the user of a laser microablation system would want to be able to vary the duration as well as the energy delivered by the system. One important reason is that a longer duration administration of the same energy can have quite different effects on tissue. As discussed above, there is in tissue both ablative and non-ablative damage. A rough differentiation between these two types of damage can be made according to whether the tissue temperature reaches the boiling point of water, in which case the damage in portions of tissue where that occurs would be ablative. Because heat is conducted away from the area where the relatively thin laser beam enters tissue, if the energy is being applied more slowly the tissue will not reach the boiling point of water and the damage will tend to be non-ablative. As discussed above and depicted in FIGS. 1-5, where non-ablative damage occurs it will tend also to have a different shape which may be more desirable in achieving the desired effect on tissue.

In addition to varying the duration during which the optical power is applied, control over the optical power may also be used to apply initially the normal high power pulse of optical energy which the laser natively produces, followed by a selected period of sub-ablation energy. The sub-ablation energy as discussed above produces a different kind of alteration of tissue from the initial pulse. This alteration is referred to sometimes as "coagulation." The ability to choose a particular power level and duration following the initial high power pulse opens the way to a much more precise control of the non-ablative damage.

For cosmetic purposes, for example, it can be desired to have primarily non-ablative damage located shortly below the surface of the skin, as schematically depicted for example in FIG. 3C.

It is also possible with control over output optical power to generate, for example, double high-power pulses of optical energy separated by a period in which a non-ablative level of optical power is applied.

One method which is possible for controlling the output energy level of the laser is to place a set of attenuators at the output of the laser. For example, one could have a set of attenuators which have attenuation values of about 10%, about 20%, about 30%, about 40%, about 50%, about 60%, about 70%, about 80%, or about 90%. Alternatively, one could have an arrangement in which a smaller number of attenuators is employed with two or more attenuators being put in the path of the beam in order to achieve a greater degree of attenuation than what one attenuator can produce.

Figure 11A:
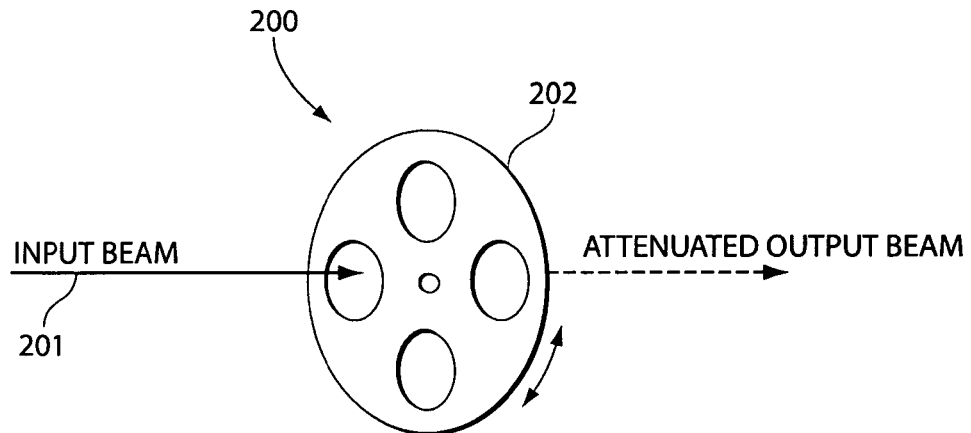
FIGS. 11A-11C depict schematically various attenuator arrangements.
Figure 11B:
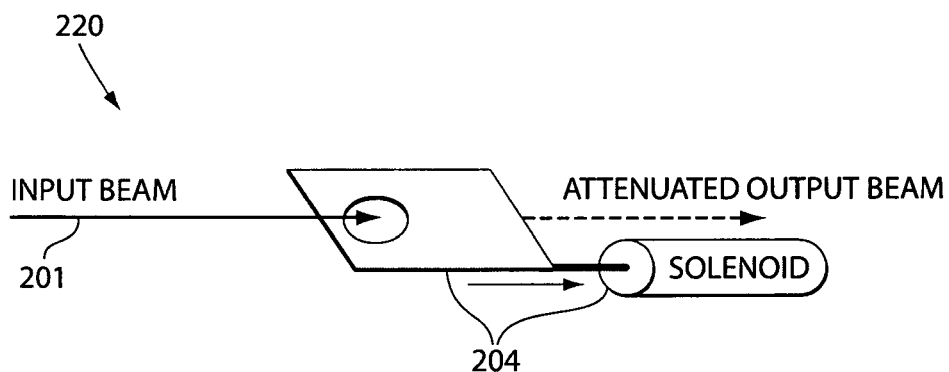
Figure 11C:
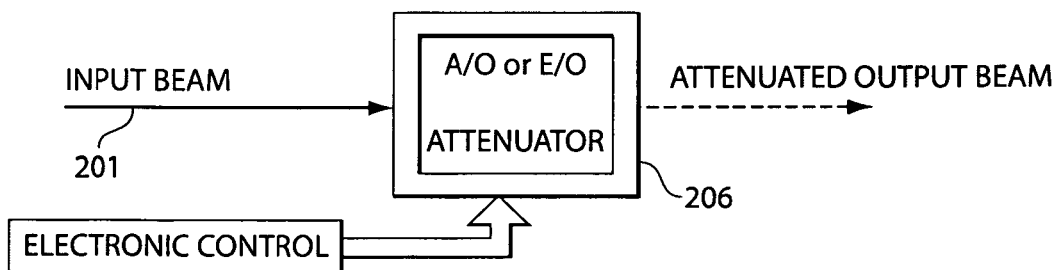

A variety of mechanical arrangements may be employed to place an attenuator in the path of the laser beam. For example, referring to FIG. 11A, a rotational arrangement 200 may include a shaft (not shown) that moves until an attenuator 202 is in place and then moves to take the attenuator 202 out of the path of the laser beam 201. Alternatively, as shown in FIG. 11B, a solenoid-based arrangement 220 may involve linear motion of an attenuator 204 in the laser beam path 201. With the rotational arrangement, a number of different attenuators of different degrees of attenuation can be attached to the shaft and the appropriate attenuator rotated into place.

In a system with a fixed set of attenuation percentages, the system might for example choose the percentage which is closest to that calculated as described above and utilize that percentage. Alternatively, the system might modify the time duration somewhat from the desired duration to achieve the exact energy chosen by the user with that closest feasible attenuation. Alternatively, the system might choose the smallest attenuation percentage which is greater than that calculated as described above, or the largest attenuation which is less than that calculated as described above.

Attenuators for light are known in the art. The precise form and structure of the attenuator for use with a laser microablation system will depend very much on the wavelength of the laser output, because different materials have different frequency responses over the broad range of frequencies for which lasers are available. The laser used in a laser microablation system will generally output a fairly narrow wavelength range corresponding to the set of wavelengths of transitions that take place as part of the laser action. For example, $CO_2$ lasers produce light at wavelengths from about 9 tim to about 11 [tin. The strongest light output from a $CO_2$ laser will tend to be at about 10.6 p.m. The precise form and structure of the attenuator will also depend on the optical power level being used, for example milliwatts or watts or hundreds of watts, since the attenuator itself should not be altered by the energy which it is absorbing. For $CO_2$ and other relatively powerful infrared lasers metal screens work well as attenuators.

In addition to attenuators which have a fixed degree of attenuation such as 60%, it is also possible to employ attenuators that have a degree of attenuation which is electronically controllable. Commercial acousto-optic and electro-optic modulators 206 are available, for example.

In an alternative technique for varying both duration and light energy provided by a laser microablation system, it is possible to turn the energy of the laser's pumping system on and off repeatedly. For example, in the case of a gas laser system which creates a population inversion by delivering DC or RF electrical energy through electrodes to a gas, the delivery of DC or RF electrical energy can be turned on and off repeatedly.

If the times at which the pumping energy is turned off and then turned back on are chosen appropriately, it is possible to operate the laser system at a chosen average optical power output well below the peak power, e.g., via pulse width modulation. It is possible, for example, to operate the system between about 1% and about 100% of peak power, or between about 10% and about 100% of peak power, with optical power output being chosen as desired.

Figure 9:
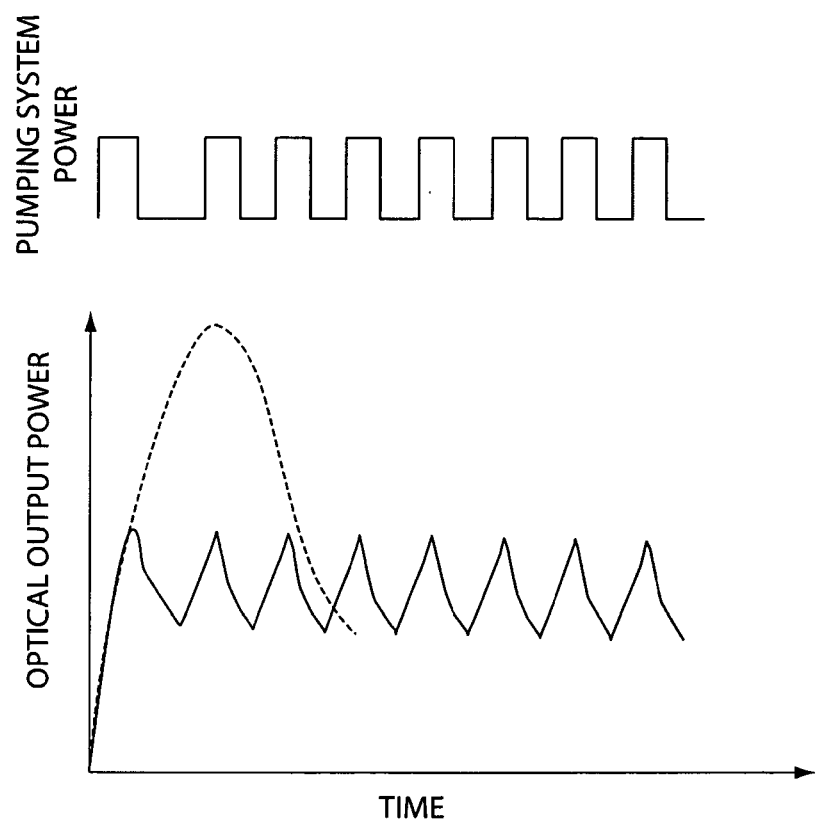
FIG. 9 depicts schematically a way to control optical output power of a laser by turning the pumping system power on and off.

The duty cycle applied to the pumping system may vary, for example, between about 20% and about 80%, or between about 40% and about 60%. Frequencies up to about 50 kHz are conveniently employed for turning on and off the pumping system power. FIG. 9 depicts schematically how one can control optical output power by turning the pumping system power on and off In that figure we see in dashed lines the initial transient as depicted in FIG. 8. We also see above the pumping system power as it is turned on and off. We see the resulting system optical output power oscillating around a power level substantially lower than the peak.

Figure 10:
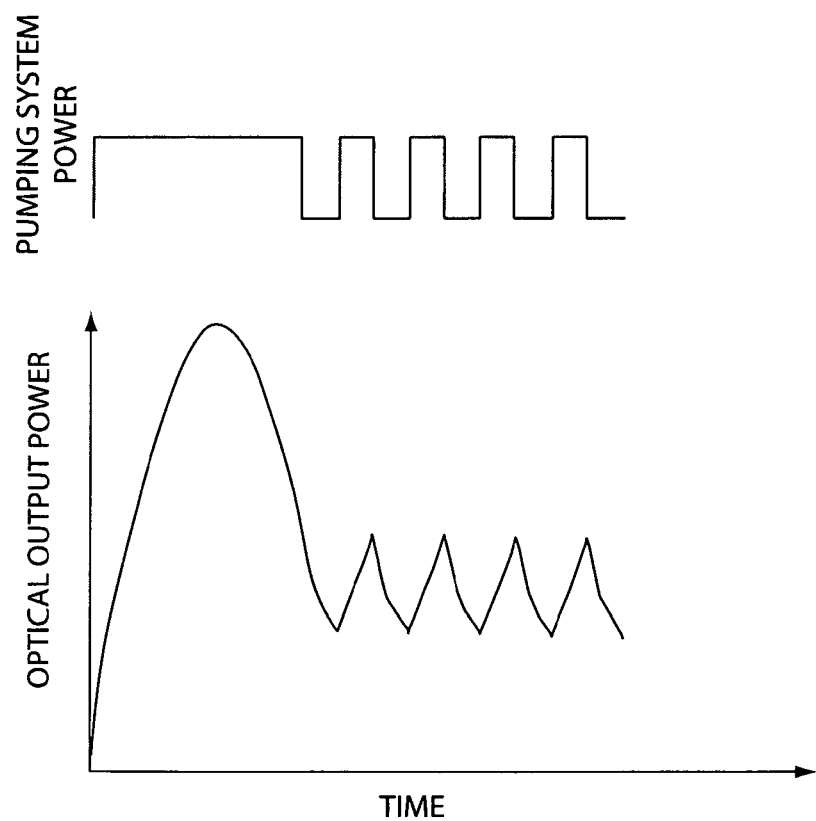
FIG. 10 depicts schematically the use of pumping system power control to apply initially the normal high power pulse of optical energy which the laser natively produces, followed by a selected period of sub-ablation energy.

FIG. 10 depicts the use of pumping system power control to apply initially the normal high power pulse of optical energy which the laser natively produces, followed by a selected period of sub-ablation energy. We see that the pumping system energy is initially turned on and held on so that the normal high power pulse is produced. After a period of time, the periodic turning on and off begins so as to produce the period of sub-ablation energy.

There are various ways to decide when to turn the pumping power on and off in order to produce a desired optical output power. With equipment in place for measuring the optical output power of the system, it would be possible to use a feedback loop in which, for example, the times of the on-off and off-on transitions in the pumping system power are varied in order to maintain the average light power output close to the precise level desired, or for other control purposes. Any of a wide variety of feedback control algorithms known to persons of skill in the art may be employed. Reference may be made, for example, to Gene Franklin et al., Feedback Control of Dynamic Systems (6th ed. 2009). Control could be, for example, a simple thermostat-like control in which power to the pumping system is turned off when instantaneous output optical power exceeds the desired level plus a percentage, and turned back on when instantaneous output optical power falls below the desired level plus a percentage. More complicated feedback controls in which, for example, the total energy delivered so far is computed and influences the decision to turn the power to the pumping system on or off may also be employed.

One may, alternatively, simply choose empirically the first turn-off time and the duty cycle to achieve each of a range of desired optical output powers with the laser in a particular system or with representative such lasers, and then program those times and duty cycles into the system's electronics for subsequent use in the field. Alternatively, one might use a measured transient output power waveform in response to an energy square wave applied to the pumping system. This measurement will produce a turn-on transient waveform and a turn off transient waveform. These waveforms may be characterized, for example, by time constants. For the turn-off transient, the time constant might be, for example, the time required for the waveform to fall to ½ of its original value. One could assume that, with on-off control of the pumping system input, the transient after the first turn-off will follow the measured turn-off transient and the transient after the first turn-on will follow the measured turn-on transient, and so choose a first turn-off time and duty cycle such that the output power predicted with the assumption will oscillate around a desired output power.

With the use of on-off driving of the pumping system power as described above, it is possible that there would be substantial fluctuation in the output power of the laser about the desired average power. Such fluctuation is generally not problematic in applications involving tissue ablation, since the thermal time constant of tissue is approximately 1 ms, and so fluctuations above approximately 1 kHz do not have a significant thermal effect.

Nonetheless, if it is desired to reduce fluctuations in the optical power output when using on-off driving of the pumping system, one way to achieve this would be to increase the frequency of the on-off driving waveform, reducing the ripple in the optical power output.

EXAMPLE

It is to be understood that the following example of the present invention is not intended to restrict the present invention since many more modifications may be made within the scope of the claims without departing from the spirit thereof.

A study was conducted that consisted of two research criteria. The first criterion evaluated different laser energy doses on 47 consecutive samples of skin. The doses ranged from 5 m.T to 200 mJ. The width and depth of the ablated "column" was measured as well as the surrounding width and depth of necrosis. The second criterion compared the effects of doses ranging from 5 mJ to 20 mJ on the arms of selected volunteers. These evaluations were recorded immediately after the firing of the laser; at one hour; one day and four days.

Summary of Results or Findings

The depth and diameter of the ablated columns correlated in a linear fashion with the dose. The column depth could be directly controlled and ranged from 180 to 1378 microns, depending on the dose level. Despite the wide range of dosing parameters, the column diameter was tightly confined and only ranged from 34-106 microns with most of column diameters being in the 50-70 micron range. Necrosis depth ranged from 27-213 microns. Necrosis width was extremely confined and ranged only from 19-55 microns. Histologically, the ablated columns produced by 5 mJ and 10 mJ pulses reached the mid- to deep-dermis; columns only penetrated to the fat at the highest dose (200 mJ). On doses of 5, 10, and 20 mJ, the resultant skin erythema and edema was evident at 1-2 days, but the mild to moderate erythema faded by the fourth day. There were no cases of necrosis.

Conclusions Reached

Utilizing histologic evaluation, it is a novel carbon dioxide based microablation device can produce selective digital injury to dermal collagen using very low energy levels. The collateral necrosis is very limited. Preliminary clinical evaluation using low energy doses demonstrates mild to moderate erythema that fades at four days. These findings will be used to determine the dosing for future clinical studies.

Although the particular embodiments shown and described above will prove to be useful in many applications in the skin treatment art to which the present invention pertains, further modifications of the present invention will occur to persons skilled in the art. All such modifications are deemed to be within the scope and spirit of the present invention as defined by the appended claims.

Example 1

It is to be understood that the following example of the invention is not intended to restrict or to limit the invention because many more modifications may be made within the scope of the claims without departing from the spirit thereof.

A study was conducted that consisted of two research criteria. The first criterion evaluated different laser energy doses on 47 consecutive samples of skin. The doses ranged from 5 mJ to 200 mJ. The width and depth of the ablated "column" was measured as well as the surrounding width and depth of necrosis. The second criterion compared the effects of doses ranging from 5 mJ to 20 mJ on the arms of selected volunteers. These evaluations were recorded immediately after the firing of the laser; at one hour; one day and four days.

Summary of Results or Findings

The depth and diameter of the ablated columns correlated in a linear fashion with the dose. The column depth could be directly controlled and ranged from 180 to 1378 microns, depending on the dose level. Despite the wide range of dosing parameters, the column diameter was tightly confined and only ranged from 34-106 microns with most of column diameters being in the 50-70 micron range. Necrosis depth ranged from 27-213 microns. Necrosis width was extremely confined and ranged only from 19-55 microns. Histologically, the ablated columns produced by 5 mJ and 10 mJ pulses reached the mid- to deep-dermis; columns only penetrated to the fat at the highest dose (200 mJ). On doses of 5, 10, and 20 mJ, the resultant skin erythema and edema was evident at 1-2 days, but the mild to moderate erythema faded by the fourth day. There were no cases of necrosis.

Conclusions Reached

Utilizing histologic evaluation, it is a novel carbon dioxide based microablation device can produce selective digital injury to dermal collagen using very low energy levels. The collateral necrosis is very limited. Preliminary clinical evaluation using low energy doses demonstrates mild to moderate erythema that fades at four days. These findings will be used to determine the dosing for future clinical studies.

Although the particular embodiments shown and described above will prove to be useful in many applications in the skin treatment art to which the present invention pertains, further modifications of the present invention will occur to persons skilled in the art. All such modifications are deemed to be within the scope and spirit of the present invention as defined by the appended claims.

Example 2

The following descriptions of the invention are provided as illustrative examples only and are not intended to limit or to restrict the invention. It is to be understood that the following examples of the invention are not intended to restrict or to limit the invention because many more modifications may be made within the scope of the claims without departing from the spirit thereof.

Figure 12A:
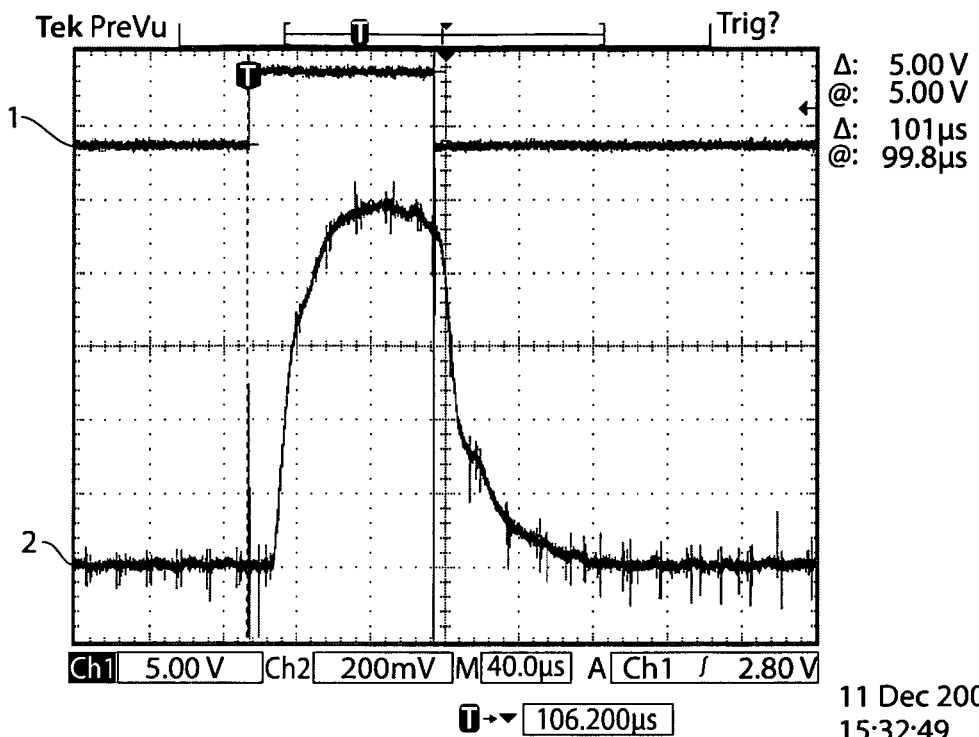
FIGS. 12A-12F depict graphical representations of laser waveforms.

Referring to FIGS. 12A-12F, a demonstration of the "pulse width modulation" techniques is described and FIGS. 12A-12F provide graphs illustrating laser output responses to control inputs. By modulating the control to the laser, one can turn the pumping system on and off, turning a high power $CO_2$ laser into a low average power laser. A lab demonstration was constructed with different pulse train structures to demonstrate different modulated laser output profiles which may result in a controlled thermal response. FIG. 12A illustrates a typical output of a high powered $CO_2$ laser. The upper waveform, identified as #1 in the graph, is the control input and the lower waveform, identified as #2 in the graph, is the laser output. The high power nature of the laser output to a typical control is shown.

With this waveform, one would expect the thermal response depicted in FIG. 1.

Figure 12B:
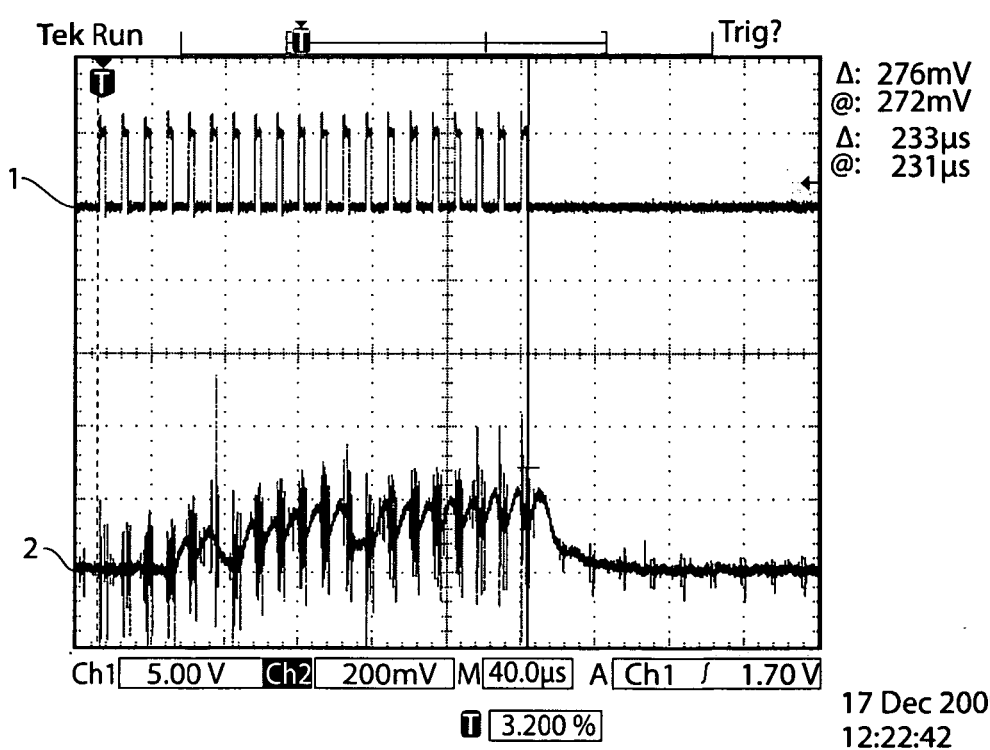

The graph of FIG. 12B shows a typical output of a high powered $CO_2$ laser with a modulated control resulting in a low average power output. The upper waveform, labeled #1 in the graph, is the control input and the lower waveform, labeled #2 in the graph, is the laser output. The low power nature of the laser output to this modulated control is shown. With this waveform, one would expect the thermal response depicted in FIG. 2A.

Figure 12C:
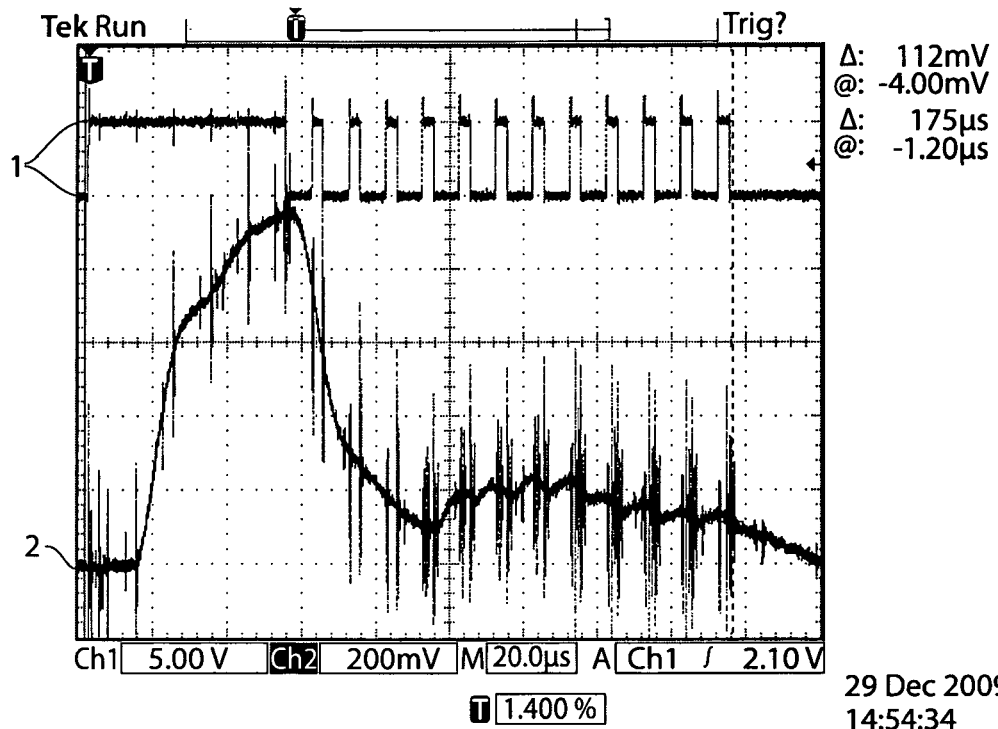

FIG. 12C illustrates a graph that shows an output of a high powered CO2 laser. The upper waveform, labeled #1 in the graph, is the control input and the lower waveform, labeled #2 in the graph, is the laser output. This graph shows the variable nature of the pulse shape due to the control modulation of varying duty cycles and duration. The high power exposure of the laser output followed with a low power exposure is shown. With this waveform one would expect the thermal response depicted in FIG. 2D.

Figure 12D:
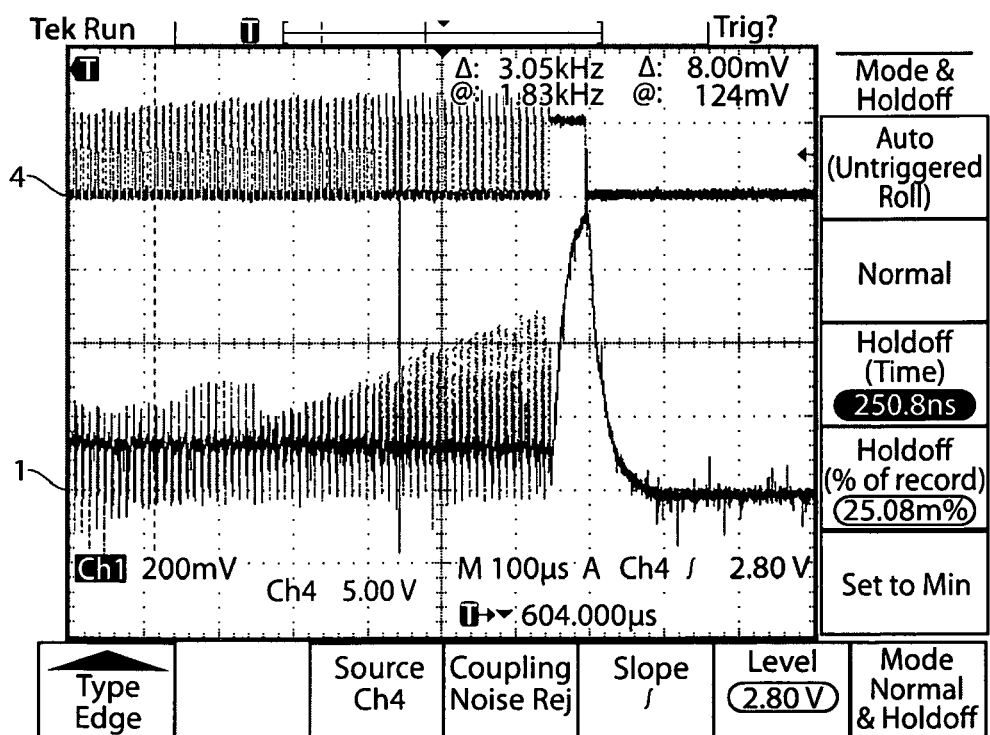

The graph of FIG. 12D shows the output of a high powered CO2 laser. The upper waveform, labeled #4 in the graph, is the control input and the lower waveform, labeled #1 is the laser output. In this example, the variable nature of the pulse shape due to the control modulation of varying duty cycles and duration is illustrated. In contrast to FIG. 12C, the low power exposure of the laser output followed with a high power exposure is shown. With this waveform one would expect the thermal response depicted in FIG. 2B.

Figure 12E:
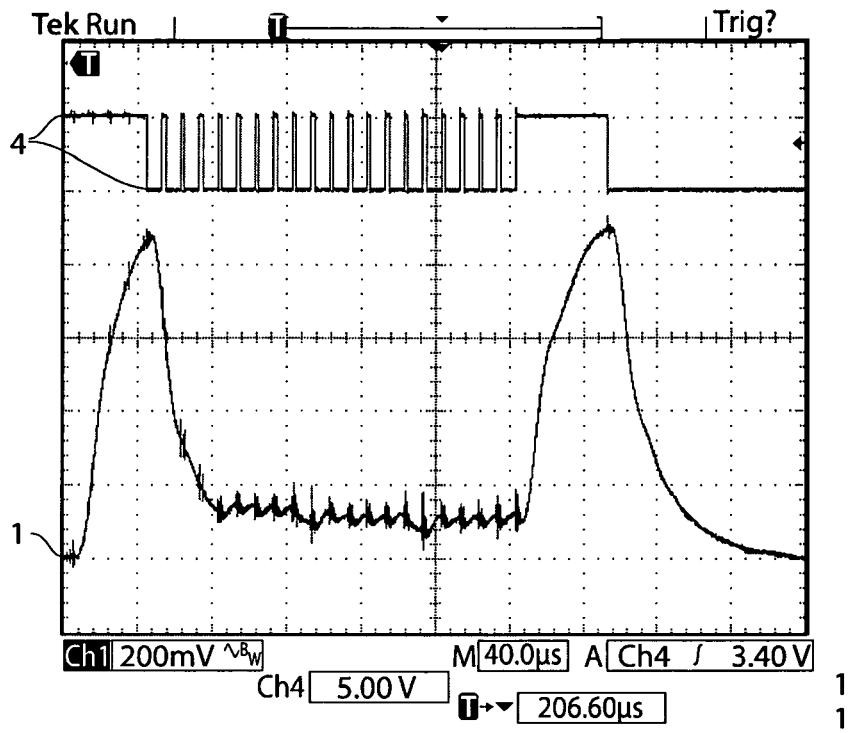

FIG. 12E illustrates a graph indicating one of the more unique outputs of a modulated high powered CO2 laser. The upper waveform, labeled #4 in the graph, is the control input and the lower waveform, labeled #1 is the laser output. In this example, the variable nature of the pulse shape due to the control modulation of varying duty cycles and duration is shown. The high power exposure of the laser output is followed with a low power exposure and followed with another high power exposure. With this waveform one would expect the thermal response depicted in FIG. 3B.

Figure 12F:
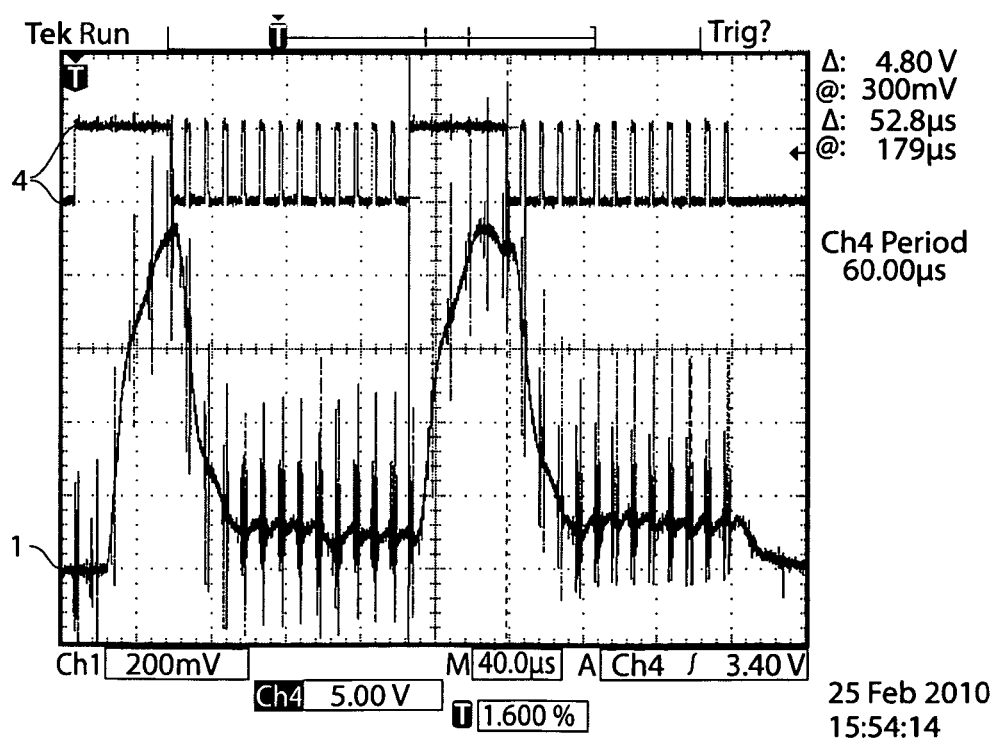

The graph of FIG. 12F shows one of the more unique outputs of a modulated high powered CO2 laser. The upper waveform, labeled #4 in the graph, is the control input and the lower waveform, labeled #1 is the laser output. In this example, one can see the variable nature of the pulse shape due to the control modulation of varying duty cycles and duration. The high power exposure of the laser output is followed with a low power exposure and followed with another high power exposure followed with another low power exposure. With this waveform one would expect the thermal response depicted in FIG. 3C.

Example 3

The following description of the invention is provided as an illustrative example only and is not intended to limit or to restrict the invention. It is to be understood that the following example of the invention is not intended to restrict or to limit the invention because many more modifications may be made within the scope of the claims without departing from the spirit thereof.

Figure 13:
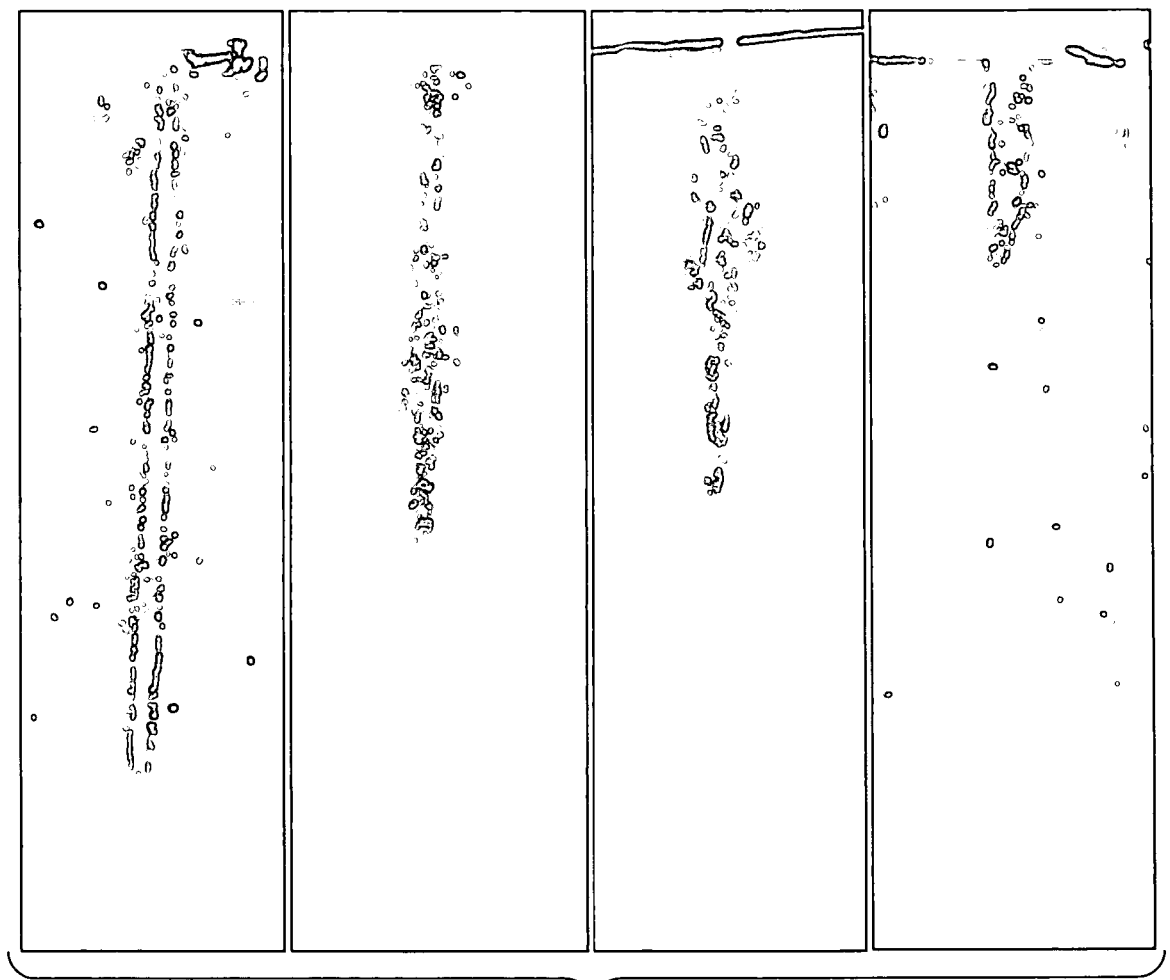
FIG. 13 is a color photograph of an irradiated polyacrylamide gel using varying laser pulse duration and power.

Referring to FIG. 12, an experiment was performed, demonstrating the effect of pulse duration and peak power on the tissue response. Three exposures of equal energy, equal spot size, but differing pulse duration were exposed into a polyacrylide gel, containing a high concentration of the target water chromophore. Left is shortest pulse (20 us), middle is a medium pulse (300 us), and right is longest pulse (1000 us). FIG. 13 demonstrates the varying depth of ablation and additional lateral thermal damage of the lower power exposures.

Conclusions Reached

High power exposures translate to deep ablation capabilities, while low power exposures ablate less and leave more thermal damage. One may conclude that, if combining low and high power combinations, one can achieve thermal damage deeper and/or vary the thermal damage zones for a multitude of depths.

Figure 14:
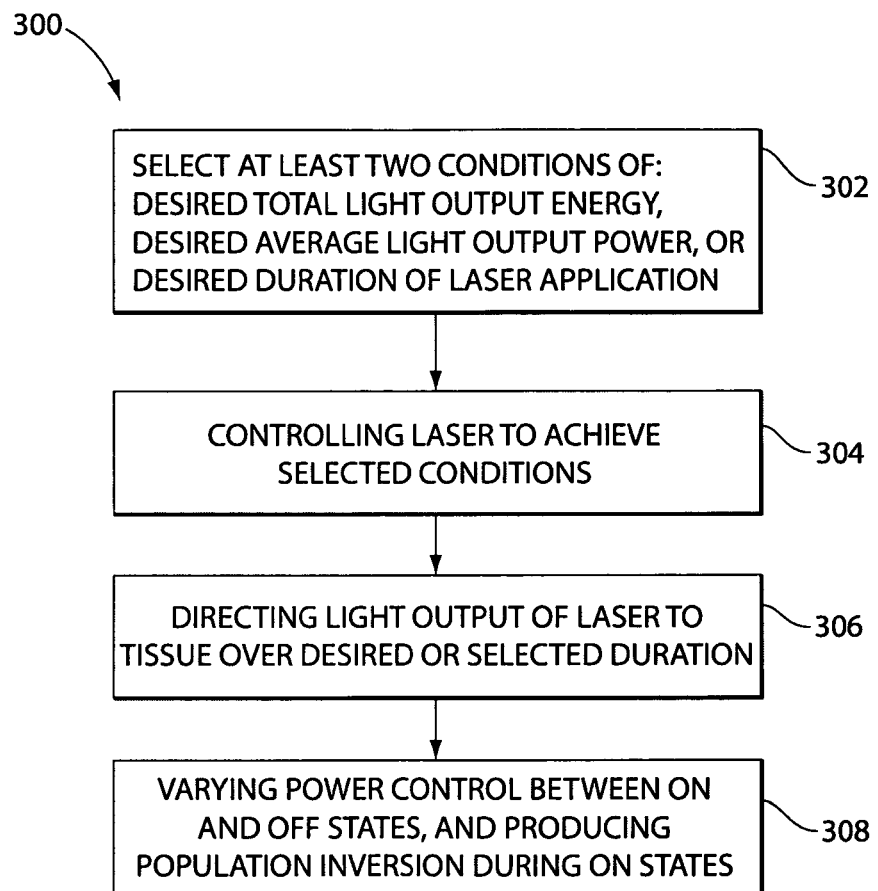
FIG. 14 is a flow diagram of a method of treating skin using a laser system with pulsed light output.

Referring to FIG. 14, in a further aspect the invention provides a method 300 for treating tissue using a laser system with pulsed light output, as described above. The method 300, however, is exemplary only and not limiting. The method 300 may be altered, e.g., by having stages added, removed or rearranged.

At phase 302, the method includes selecting at least two of: (i) a desired total light output energy, (ii) a desired average light output power, or (iii) a desired duration of laser application.

At phase 304, the method further includes controlling the laser by the system in order to achieve the selected conditions (i), (ii), or (iii) specified by the user.

At phase 306, the method includes directing the light output of the laser to the tissue to be treated over the desired duration.

At stage 308, the method includes varying a control for power, which produces a population inversion, between on and off states, such that, a population inversion may be produced when the control is varied from an off state to an on state.

It will be appreciated by persons of ordinary skill in the art that according to some embodiments of the present invention other applications according to the principles of the present invention are possible and are in the scope of this application. While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

What is claimed is:

1. A laser system comprising: a laser source; a laser emitting device coupled to the laser source and being configured to apply laser pulses to a skin tissue surface to apply treatments to the skin tissue surface;
    a controller configured to control application of the laser pulses;
    wherein the controller is further configured to: (a) move the laser emitting device to each of a plurality of sites on the skin tissue surface; and (b) direct the laser emitting device to apply at least one ablative laser pulse at each of the plurality of sites within a treatment area on the skin tissue surface to ablate a channel at each of the plurality of sites;
    further comprising an imager for imaging one or more areas on the skin tissue surface;
    an image processor associated with the imager, the imager processor being configured for processing the one or more areas of the skin tissue surface imaged by the imager;
    the imager being configured for imaging a wrinkle topography of the skin tissue;

the imager being configured to communicate the imaged wrinkle topography to the image processor, the image processor being configured to cause the controller to send a signal to the laser emitting device to cause the laser emitting device to be moved to one or more target treatment sites on the skin tissue; and, the controller then being configured to cause the laser emitting device to apply laser pulses to the one or more sites based on the wrinkle topology.

2. The laser device of claim 1, further comprising the imager and image processor being configured to measure the effectiveness of the treatment and further being configured to return the laser emitting device to one or more treatment area sites requiring additional treatment.

3. The laser system of claim 1, wherein the imager and image processor are configured to cause the controller to return the laser emitting device to one or more previously treated sites in the treatment area.

4. The laser system of claim 1, wherein the imager and image processor are configured to map the one or more of the plurality of treatment sites on the skin tissue surface, such that, if there is movement of the skin treatment surface between pulses during treatment, the controller is configured to return the laser emitting device to the position of the previous pulse.

5. The laser system of claim 1, wherein the laser source is a carbon dioxide (CO2) laser.

6. A method of treating a skin tissue surface comprising:
providing a laser system, the laser system comprising: a laser source; a laser emitting device coupled to the laser source and being configured to apply laser pulses to a skin tissue surface to apply treatments to the skin tissue surface;
providing a controller configured to control application of the laser pulses;
wherein the controller: (a) moves the laser emitting device to each of a plurality of sites on the skin tissue surface; and (b) directs the laser emitting device to apply at least one ablative laser pulse at each of the plurality of sites within a treatment area on the skin tissue surface to ablate a channel at each of the plurality of sites;
further comprising providing an imager for imaging one or more areas on the skin tissue surface;
further comprising an image processor associated with the imager, the imager processor processing the one or more areas of the skin tissue surface imaged by the imager;
the imager imaging a wrinkle topography of the skin tissue;
the imager communicating the imaged wrinkle topography to the image processor, the image processor causing the controller to send a signal to the laser emitting device to cause the laser emitting device to be moved to one or more target treatment sites on the skin tissue; and, the controller then causing the laser emitting device to apply laser pulses to the one or more sites on the skin tissue surface based on the wrinkle topology.

7. The method of claim 6, further comprising the step of the imager and image processor measuring the effectiveness of the treatment and further returning the laser emitting device to one or more treatment area sites requiring additional treatment.

8. The method of claim 6, further comprising the step wherein the imager and the image processor cause the controller to return the laser emitting device to one or more previously treated sites in the treatment area.

9. The method of claim 6, further comprising the step wherein the imager and image processor map the one or more of the plurality of treatment sites on the skin tissue surface, such that, if a patient moves between pulses during treatment, causing movement of the skin treatment surface, the controller returns the laser emitting device to the position of the previous pulse.

10. The method of claim 6, wherein the laser source is a carbon dioxide (CO2) laser.

11. A laser system comprising: a laser source; a laser emitting device coupled to the laser source and being configured to apply laser pulses to a skin tissue surface to apply treatments to the skin tissue surface;
a controller configured to control application of the laser pulses;
wherein the controller is further configured to: (a) move the laser emitting device to each of a plurality of sites on the skin tissue surface; and (b) direct the laser emitting device to apply at least one ablative laser pulse at each of the plurality of sites within a treatment area on the skin tissue surface to ablate a channel at each of the plurality of sites;
the controller further being configured to determine the density of ablated channels within the treatment area;
further comprising an imager for imaging one or more areas on the skin tissue surface;
an image processor associated with the imager, the imager processor being configured for processing the one or more areas of the skin tissue surface imaged by the imager;
the imager being configured for imaging a wrinkle topography of the skin tissue;
the imager being configured to communicate the imaged wrinkle topography to the image processor, the image processor being configured to cause the controller to send a signal to the laser emitting device to cause the laser emitting device to be moved to one or more target treatment sites on the skin tissue; and,
the controller then being configured to cause the laser emitting device to apply laser pulses to the one or more sites based on the wrinkle topology.

\* \* \* \* \*